United States Patent
Anderson et al.

(10) Patent No.: US 6,842,644 B2
(45) Date of Patent: Jan. 11, 2005

(54) USER NAVIGATION AND GUIDANCE DURING CONFIGURATION AND STORAGE OF PARAMETERS FOR MEDICAL DEVICE

(75) Inventors: Thomas N. Anderson, Issaquah, WA (US); John D. Higinbotham, Seattle, WA (US); David A. Miller, Woodinville, WA (US); Mark Schwartz, Hugo, MN (US); C. Denise Thompson, Eugene, OR (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 8 days.

(21) Appl. No.: 10/008,525

(22) Filed: Nov. 2, 2001

(65) Prior Publication Data

US 2003/0088291 A1 May 8, 2003

(51) Int. Cl.[7] .............................................. A61N 1/37
(52) U.S. Cl. ....................................................... 607/32
(58) Field of Search ..................... 607/30–32; 600/510, 600/523

(56) References Cited

U.S. PATENT DOCUMENTS

| | | | |
|---|---|---|---|
| 4,208,008 A | 6/1980 | Smith | 371/15 |
| 4,432,360 A | 2/1984 | Mumford et al. | 128/419 PG |
| 4,809,697 A | 3/1989 | Causey, III et al. | 128/419 PT |
| 5,607,460 A | 3/1997 | Kroll et al. | 607/30 |
| 5,716,382 A | 2/1998 | Snell | 607/30 |
| 5,833,623 A | 11/1998 | Mann et al. | 600/523 |
| 5,891,178 A | 4/1999 | Mann et al. | 607/27 |
| 6,014,581 A * | 1/2000 | Whayne et al. | |
| 6,088,618 A | 7/2000 | Kerver | 607/30 |
| 6,249,705 B1 | 6/2001 | Snell | 607/59 |
| 6,289,248 B1 | 9/2001 | Conley et al. | 607/59 |
| 6,393,325 B1 * | 5/2002 | Mann et al. | 607/46 |
| 6,574,511 B2 | 6/2003 | Lee | 607/60 |

FOREIGN PATENT DOCUMENTS

EP  0565084  10/1993  ......... A61B/5/0452

* cited by examiner

Primary Examiner—Scott M. Getzow
(74) Attorney, Agent, or Firm—Schwegman, Lundberg, Woessner & Kluth, P.A.

(57) ABSTRACT

Systems and methods for providing a navigation and guidance sequence during configuration, input, and storage of programmable parameters for use in a medical device. One embodiment includes a cardiac rhythm management device as the medical device. The navigational sequence provides a series of interfaces on which parameter input fields are displayed. In one embodiment, the interfaces are graphical user interfaces. Each interface may include a plurality of different sets of parameter input fields with only one set being displayed at a time.

40 Claims, 25 Drawing Sheets

CREATING A CUSTOM PARAMETER PROFILE

SELECT DESIRED PARAMETER VALUE IN THE PROFILE COLUMN.
NAVIGATE TO THE PARAMETER SCREENS AS NEEDED.
WHEN COMPLETED, SELECT "NEXT" TO PROCEED TO THE BRADY PARAMETER SCREEN.

|  | # ZONES | [145] BPM VT | [165] BPM VF |
|---|---|---|---|
| DDD | 1 | 2.5 SEC. SVI INHIBIT | 1.0 SEC. |
| 60 PPM | 2 | AIPx1 31J 31J 31Jx3 | 31J 31J 31Jx3 |
| MIR 120 PPM | 3 | | |

ATP1=BURST         VT THERAPY
                   ATP2=DISABLED                    SHOCKS

PROFILE                          PROFILE
                   541 —[ 1 ]        [OFF]          SHOCK 1    551 —[ 31 ] J
NUMBER OF BURSTS                                    SHOCK 2    552 —[ 31 ] J
PULSES PER BURST                                    SHOCKS 3-5
INITIAL            542 —[ 4 ] MS
INCREMENT          543 —[ 0 ] SEC                   ATP TIME-OUT
MAXIMUM                                             BEGIN SHOCKS AT: 555 —[1:00] MS
COUPLING INTERVAL  545 —[ 81 ] %
DECREMENT                          MS
RAMP DECREMENT     547 —[ 81 ] %
SCAN DECREMENT     548 —[ 0 ] MS
BURST CYCLE LENGTH                 MS
MINIMUM INTERVAL   549 —[ 200 ] MS (CANCEL)—450    (▼BACK)—313    (NEXT▲)—317    (FINISH▲)—321

Fig. 5B

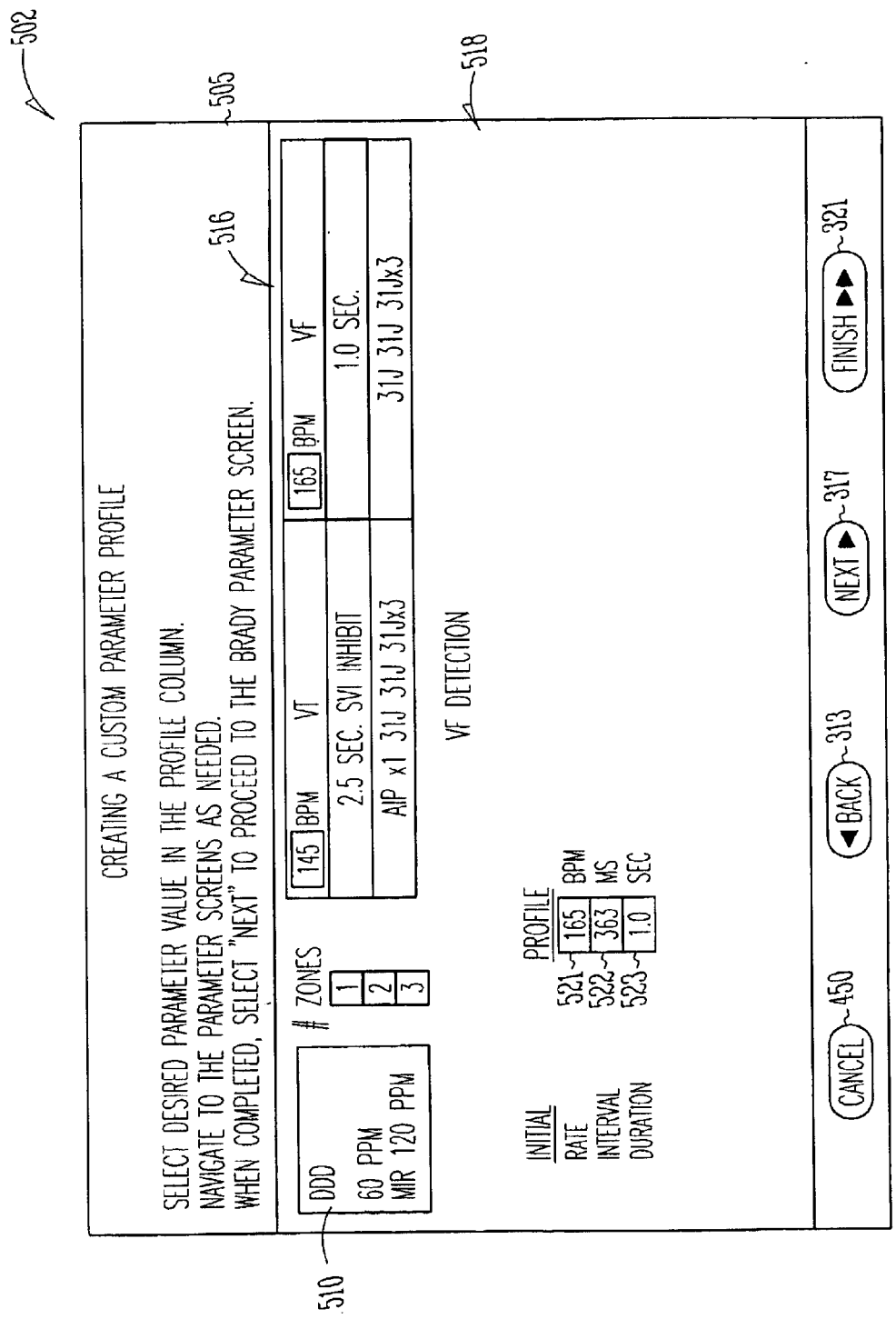

CREATING A CUSTOM PARAMETER PROFILE

SELECT DESIRED PARAMETER VALUE IN THE PROFILE COLUMN.
NAVIGATE TO THE PARAMETER SCREENS AS NEEDED.
WHEN COMPLETED, SELECT "NEXT" TO PROCEED TO THE BRADY PARAMETER SCREEN.

| DDD | # ZONES | 1 | 2 | 3 |
|---|---|---|---|---|
| 60 PPM | | | | |
| MIR 120 PPM | | | | |

| | 145 BPM | VT | 165 BPM | VF |
|---|---|---|---|---|
| | | 2.5 SEC. SVT INHIBIT | | 1.0 SEC. |
| | | AIP x1 31J 31Jx3 | | 31J 31J 31Jx3 |

VF THERAPY

|  | PROFILE |
|---|---|
| SHOCK 1 | 31 J |
| SHOCK 2 | 31 J |
| SHOCKS 3-5 | |
| # OF ADDITIONAL MAX SHOCKS | 0 |

( CANCEL )  ( ▼BACK )  ( NEXT▲ )  ( FINISH▲▲ )

Fig. 5D

CREATING A CUSTOM PARAMETER PROFILE

SELECT DESIRED PARAMETER VALUE IN THE PROFILE COLUMN.
NAVIGATE TO THE PARAMETER SCREENS AS NEEDED.
WHEN COMPLETED, SELECT "NEXT" TO PROCEED TO THE BRADY PARAMETER SCREEN.

| NORMAL | DDDR | POST-SHOCK: | DDD |

PROFILE
DDDR
MODE                          ON
A-TACHY RESPONSE
LOWER RATE LIMIT              60   PPM
MAX TRACKING RATE             120  PPM
MAX SENSOR RATE               120  PPM
AV DELAY (PACED)
ATRIAL
  PULSE WIDTH                 0.4  MS
  AMPLITUDE                   3.5  V
  REFRACTORY (PVARP)               MS
VENTRICULAR
  PULSE WIDTH                 0.4  MS
  AMPLITUDE                   3.5  V
  REFRACTORY                       MS
  *POST SHOCK DELAY           3.0  SEC
*AFFECTS NORMAL AND POST-SHOCK

| SENSOR | AV DELAY |
|--------|----------|
| TACHY RESPONSE | REFRACTORY |
| RATE ENHANCEMENTS | NOISE RESPONSE |

625

PROFILE
RATE HYSTERESIS                         OFF   PPM
HYSTERESIS OFFSET                             CYCLES
SEARCH HYSTERESIS
RATE SMOOTHING
  UP                                    OFF   %
  DOWN                                  OFF   %
MAX PACING RATE                               PPM
ATRIAL PACING PREFERENCE
MAX PACING RATE                         OFF   PPM
SEARCH INTERVAL                               CYCLES (CANCEL)~450    (▼BACK)~313    (NEXT▲)~317    (FINISH▲▲)~321

Fig. 6C

CREATING A CUSTOM PARAMETER PROFILE

SELECT DESIRED PARAMETER VALUE IN THE PROFILE COLUMN.
NAVIGATE TO THE PARAMETER SCREENS AS NEEDED.
WHEN COMPLETED, SELECT "NEXT" TO PROCEED TO THE BRADY PARAMETER SCREEN.

| NORMAL | DDDR | POST-SHOCK: | DDD |
|---|---|---|---|

| | PROFILE |
|---|---|
| MODE | DDDR |
| A-TACHY RESPONSE | ON |
| LOWER RATE LIMIT | 60 PPM |
| MAX TRACKING RATE | 120 PPM |
| MAX SENSOR RATE | 120 PPM |
| AV DELAY (PACED) | |
| ATRIAL | |
| PULSE WIDTH | 0.4 MS |
| AMPLITUDE | 3.5 V |
| REFRACTORY (PVARP) | MS |
| VENTRICULAR | |
| PULSE WIDTH | 0.4 MS |
| AMPLITUDE | 3.5 V |
| REFRACTORY | MS |
| *POST SHOCK DELAY | 3.0 SEC |

*AFFECTS NORMAL AND POST-SHOCK

| SENSOR | AV DELAY |
|---|---|
| TACHY RESPONSE | REFRACTORY |
| RATE ENHANCEMENTS | NOISE RESPONSE |

| | PROFILE |
|---|---|
| DYNAMIC AV DELAY | ON |
| MAXIMUM DELAY | 180 MS |
| MINIMUM DELAY | 80 MS |
| SENSED AV OFFSET | OFF MS |
| AV SEARCH HYSTERESIS | |
| SEARCH INTERVAL | OFF CYCLES |
| AV INCREASE | % |

( CANCEL )—450   ( ◀BACK )—313   ( NEXT▲ )—317   ( FINISH▲▲ )—321

Fig. 6D

CREATING A CUSTOM PARAMETER PROFILE

SELECT DESIRED PARAMETER VALUE IN THE PROFILE COLUMN.
NAVIGATE TO THE PARAMETER SCREENS AS NEEDED.
WHEN COMPLETED, SELECT "NEXT" TO PROCEED TO THE BRADY PARAMETER SCREEN.

| NORMAL | DDDR | POST-SHOCK: | DDD |
|---|---|---|---|

| | PROFILE |
|---|---|
| MODE | DDDR |
| A-TACHY RESPONSE | ON |
| LOWER RATE LIMIT | 60 PPM |
| MAX TRACKING RATE | 120 PPM |
| MAX SENSOR RATE | 120 PPM |
| AV DELAY (PACED) | |
| ATRIAL | |
| PULSE WIDTH | 0.4 MS |
| AMPLITUDE | 3.5 V |
| REFRACTORY (PVARP) | MS |
| VENTRICULAR | |
| PULSE WIDTH | 0.4 MS |
| AMPLITUDE | 3.5 V |
| REFRACTORY | MS |
| *POST SHOCK DELAY | 3.0 SEC |

*AFFECTS NORMAL AND POST-SHOCK

| SENSOR | AV DELAY |
|---|---|
| TACHY RESPONSE | REFRACTORY |
| RATE ENHANCEMENTS | NOISE RESPONSE |

| | PROFILE |
|---|---|
| DYNAMIC PVARP | ON |
| MAXIMUM PVARP | 250 MS |
| MINIMUM PVARP | 240 MS |
| PVARP AFTER PVC | 400 MS |
| DYNAMIC VRP | ON |
| MAXIMUM VRP | 250 MS |
| MINIMUM VRP | 240 MS |
| V-BLANK AFTER A-PACE | 65 MS |
| A-BLANK AFTER V-PACE | 85 MS |
| A-BLANK AFTER V-SENSE | SMART MS |

(CANCEL) 450 (▼BACK) 313 (NEXT ▲) 317 (FINISH ▲▲) 321

Fig. 6E

CREATING A CUSTOM PARAMETER PROFILE

SELECT DESIRED PARAMETER VALUE IN THE PROFILE COLUMN.
NAVIGATE TO THE PARAMETER SCREENS AS NEEDED.
WHEN COMPLETED, SELECT "NEXT" TO PROCEED TO THE BRADY PARAMETER SCREEN.

| NORMAL | DDDR | POST-SHOCK: | DDD |
|--------|------|-------------|-----|

PROFILE
MODE                    [DDDR]
A-TACHY RESPONSE         ON
LOWER RATE LIMIT         [60] PPM
MAX TRACKING RATE        [120] PPM
MAX SENSOR RATE          [120] PPM
AV DELAY (PACED)
ATRIAL
  PULSE WIDTH            [0.4] MS
  AMPLITUDE              [3.5] V
  REFRACTORY (PVARP)         MS
VENTRICULAR
  PULSE WIDTH            [0.4] MS
  AMPLITUDE              [3.5] V
  REFRACTORY                 MS
*POST SHOCK DELAY        [3.0] SEC

*AFFECTS NORMAL AND POST-SHOCK

| SENSOR | AV DELAY |
|--------|----------|
| TACHY RESPONSE | REFRACTORY |
| RATE ENHANCEMENTS | NOISE RESPONSE |

*NOISE RESPONSE

PROFILE
[DDD]

(CANCEL)~450  (▼BACK)~313  (NEXT▲)~317  (FINISH▲▲)~321

Fig. 6H

CREATING A CUSTOM PARAMETER PROFILE

SELECT DESIRED PARAMETER VALUE IN THE PROFILE COLUMN.
NAVIGATE TO THE PARAMETER SCREENS AS NEEDED.
WHEN COMPLETED, SELECT "NEXT" TO PROCEED TO THE BRADY PARAMETER SCREEN.

ARRHYTHMIA LOGBOOK SETUP – EPISODES/EGM

| | PROFILE |
|---|---|
| *EPISODE DATA STORAGE | |
| TACHY | 80 % |
| EGM STORAGE | 5:04 M:S |
| BRADY (AIR AND PMI) | 80 % |
| AIR EGM STORAGE | 1:16 M:S |
| *INCLUDES EPISODE DETAIL, EGM, AND INTERVALS | |
| ELECTROGRAM STORAGE SOURCE | |
| ATRIAL | ON |
| VENTRICULAR | ON |
| SHOCK | ON |
| ADDITIONAL FEATURES | |
| NONSUSTAINED EPISODE STORAGE | ON |
| VF PRIORITY PROTECTION | ON |
| ONSET EGM STORAGE | ON |
| PMI EPISODE STORAGE | ON |

MAGNET BEEPER
EPISODES/ EGM
PATIENT TRIGGERED
TRENDING
SENSITIVITY ADJUSTMENT
DAILY MEASUREMENT
THERAPY FEATURES

CANCEL — 450    ◄BACK — 313    NEXT▲ — 317    FINISH▲▲ — 321

Fig. 7B

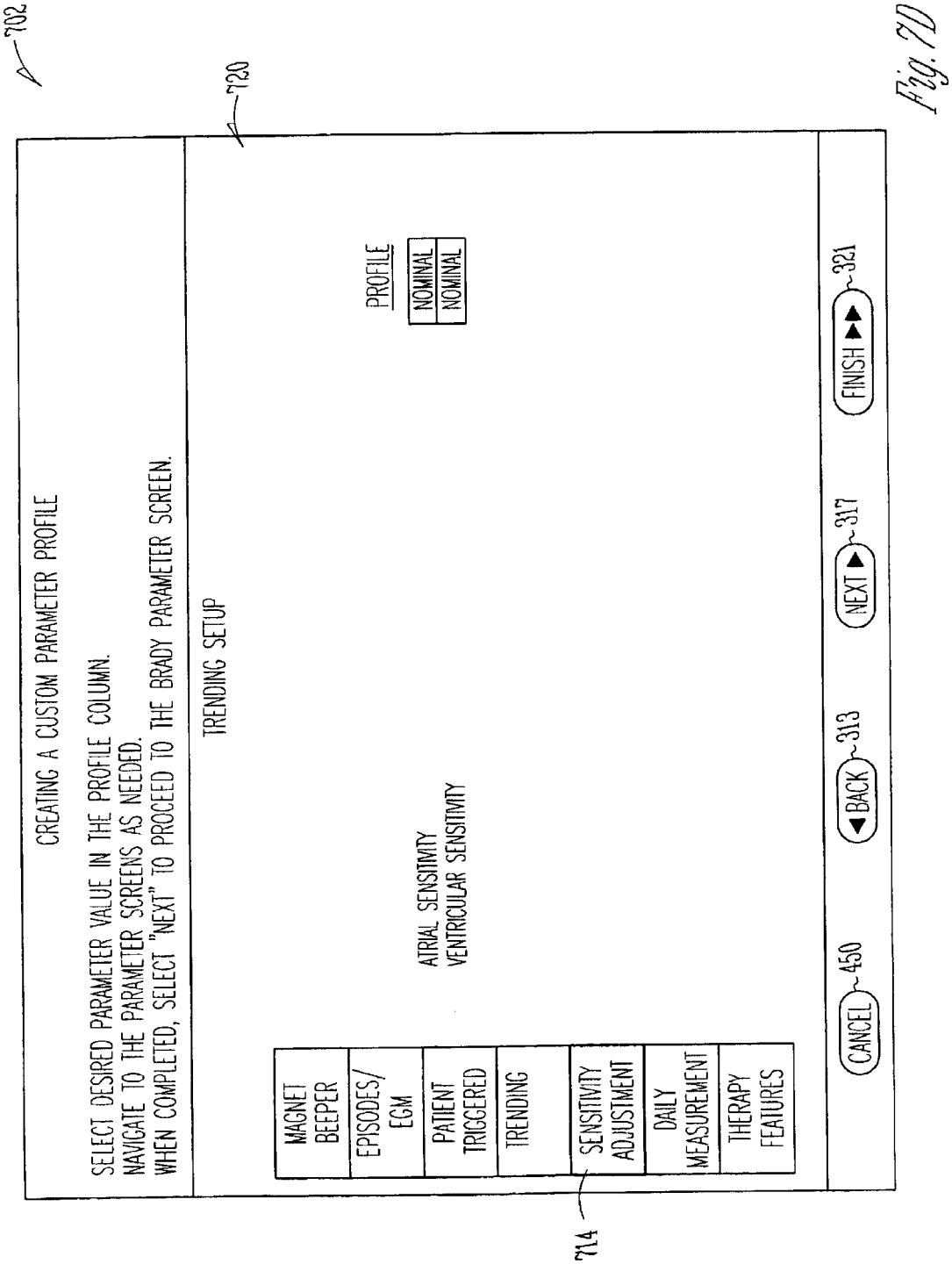

CREATING A CUSTOM PARAMETER PROFILE

SELECT DESIRED PARAMETER VALUE IN THE PROFILE COLUMN.
NAVIGATE TO THE PARAMETER SCREENS AS NEEDED.
WHEN COMPLETED, SELECT "NEXT" TO PROCEED TO THE BRADY PARAMETER SCREEN.

DAILY MEASUREMENT SETUP

| | PROFILE |
|---|---|
| ATRIAL INTRINSIC AMPLITUDE | ON |
| MINIMUM | 1 MV |
| MAXIMUM | 25 MV |
| VENTRICULAR INTRINSIC AMPLITUDE | ON |
| MINIMUM | 3 MV |
| MAXIMUM | 25 MV |
| ATRIAL PACE IMPEDANCE | ON |
| MINIMUM | 250 Ω |
| MAXIMUM | 2500 Ω |
| VENTRICULAR PACE IMPEDANCE | ON |
| MINIMUM | 250 Ω |
| MAXIMUM | 2500 Ω |
| SHOCK IMPEDANCE | ON |
| MINIMUM | 20 Ω |
| MAXIMUM | 80 Ω |

- MAGNET BEEPER
- EPISODES/EGM
- PATIENT TRIGGERED
- TRENDING
- SENSITIVITY ADJUSTMENT
- DAILY MEASUREMENT
- THERAPY FEATURES (CANCEL)~450  (▼BACK)~313  (NEXT▲)~317  (FINISH▲)~321

Fig. 7E

CREATING A CUSTOM PARAMETER PROFILE

INCLUDE THESE CLINICAL EVENTS:

- [✓] TACHY-MODE (IF OTHER THAN MONITOR + THERAPY)
- [✓] BATTERY AT EOL, EBI
- [✓] NUMBER OF V-TACHY EPISODES SINCE (DATE)
- [✓] LAST V-TACHY EPISODES ON (DATE)
- [ ] NUMBER OF AIR SWITCHES SINCE (DATE) ............ EVENT THRESHOLD [ 1 ]
- [✓] *SHOCK IMPEDANCE OUT OF RANGE
- [✓] *PACE IMPEDANCE OUT OF RANGE
- [✓] *INTRINSIC AMPLITUDE OUT OF RANGE
- [✓] PMI EVENTS ............ EVENT THRESHOLD [ 1 ]
- [✓] PATIENT TRIGGERED EVENT STORED/ACTIVE
- [ ] NUMBER OF NONSUSTAINED EVENTS SINCE (DATE) ............ EVENT THRESHOLD [ 1 ]

*ADJUST PATIENT SPECIFIC THRESHOLDS IN DAILY MEASUREMENTS.

(CANCEL)~950A    (▼BACK)~913A    (NEXT▲)~917A    (FINISH▲)~921

Fig. 9A

CREATING A CUSTOM PARAMETER PROFILE

INCLUDE IN QUICK NOTES REPORT:

- ☑ THERAPY HISTORY (RECENT EPISODES)
- ☑ EPISODE COUNTERS- TACHY/BRADY
- ☑ TACHY PARAMETER SUMMARY
- ☑ BRADY PARAMETER SUMMARY
- ☑ MAGNET CONFIGURATION
- ☑ DEVICE DATA (STATUS INFORMATION ON BATTERY, CAP REFORM,...)
- ☑ MEASURED DATA (IMPLANT AND FOLLOW-UP MEASUREMENTS)
- ☑ HISTOGRAMS
- ☑ DAILY MEASURED GRAPHS (AMPLITUDE AND IMPEDANCE MEASUREMENTS)
- ☑ TRENDING GRAPH (CANCEL)~450  (▼BACK)~913B  (NEXT▲)~917B  (FINISH▲▲)~321

Fig. 9B  ~902B

CREATING A CUSTOM PARAMETER PROFILE

SELECT QUICK CHECK VR TESTS:
- ☑ INTRINSIC AMPLITUDE TEST
- ☑ PACE IMPEDANCE TEST
- ☑ SHOCK IMPEDANCE TEST
- ☑ VENTRICULAR THRESHOLD TEST

☑ PRINT THRESHOLD SNAPSHOTS
☐ PRINT QUICK NOTES
  # OF COPIES [ 1 ]
☐ SAVE ALL TO DISK
☐ RESET COUNTERS

SELECT QUICK CHECK VR START VALUES:

| USE SMARTSTART VALUES | SELECT PROFILE VALUES |

─ INTRINSIC AMPLITUDE TEST ─
MODE
LOWER RATE                PPM

─ PACE THRESHOLD TEST ─
TEST TYPE
| AMPLITUDE |
| PACE WIDTH |

MODE
LOWER RATE            PPM
*AMPLITUDE            V
*PULSE WIDTH          MS

*SMARTSTART PRESELECTS THRESHOLDS.

(CANCEL)~450   (▼BACK)~913C   (NEXT▲)~917C   (FINISH▲▲)~321

CREATING A CUSTOM PARAMETER PROFILE

SELECT QUICK CHECK DR TESTS:

- ☑ INTRINSIC AMPLITUDE TEST
- ☑ PACE IMPEDANCE TEST
- ☑ SHOCK IMPEDANCE TEST
- ☑ ATRIAL THRESHOLD TEST
- ☑ VENTRICULAR THRESHOLD TEST

☑ PRINT THRESHOLD SNAPSHOTS
☐ PRINT QUICK NOTES   # OF COPIES [1]
☐ SAVE ALL TO DISK
☐ RESET COUNTERS

SELECT QUICK CHECK VR START VALUES:

[ USE SMARTSTART VALUES ]   [ SELECT PROFILE VALUES ]

INTRINSIC AMPLITUDE TEST
CHAMBER TESTED
| ATRIUM | MODE |  |
| VENTRICLE | LOWER RATE | PPM |
|  | AV DELAY | MS |

PACE THRESHOLD TEST
TEST TYPE
[ AMPLITUDE ]
[ PACE WIDTH ]

MODE
LOWER RATE                PPM
*AMPLITUDE                V
*PULSE WIDTH              MS

*SMARTSTART PRESELECTS THRESHOLDS.

PACE IMPEDANCE TEST
CHAMBER TESTED
| ATRIUM |
| VENTRICLE |

( CANCEL )~450    ( ▼BACK )~913D    ( NEXT▲ )~917D    ( FINISH▲▲ )~321

*Fig. 9D*

USER NAVIGATION AND GUIDANCE DURING CONFIGURATION AND STORAGE OF PARAMETERS FOR MEDICAL DEVICE

FIELD OF THE INVENTION

The present system and method relates to user navigation and guidance during configuration of stored parameters for a medical device and, more particularly, to a user guidance and navigational method and aide device for setting up profiles of stored parameters for a cardiac rhythm management device.

BACKGROUND

Cardiac rhythm management systems provide therapy to a patient's heart to correct various forms of arrhythmias, such as tachyarrhythmias and bradyarrhythmias. One type of these systems includes an implantable cardiac rhythm management ("CRM") device and a programmer for programming the CRM device. As the understanding of various types of arrhythmias has grown since the inception of CRM devices, so has the need to provide a greater variety of therapies with the CRM device. This greater variety of therapies allows a physician to closely tailor the therapy provided by the CRM device to the specific needs of the patient by programming various parameters of the CRM device. However, the number of programmable parameters in CRM devices has grown along with the number and complexity of therapies that an individual CRM device can provide. Additionally, not all parameters that can be programmed are necessary or even appropriate for certain therapies. Accordingly, the physician uses the programmer to program numerous parameters of the CRM device to achieve the desired therapy while ignoring other parameters unrelated to the present therapy. It is thus desirable to store profiles containing all programmed parameters for certain therapies and for select patients. There is a learning curve for learning the system, e.g., hardware and software, to program the parameter profiles that are appropriate for a given therapy. The numerous parameters further increase the time it takes to learn how to program the parameters in the profiles. Consequently, there is a need in the field of CRM systems to simplify the programming of profiles containing parameters for the CRM device by providing user friendly navigation and guidance to facilitate efficient parameter and profile programming. Moreover, there is a need to provide efficient navigation through the process of programming profiles both in a forward direction (to the end) and a reverse direction (toward the beginning) so that the profile can be reviewed and updated as necessary.

SUMMARY OF THE INVENTION

The present system includes a programmer including a navigational sequence that provides navigation and guidance to the medical personnel inputting the parameters for a medical device such as a cardiac rhythm management device. The navigational sequence displays a sequence of interfaces in any of which the user may enter information specific to the interface. Progression through the prescribed navigational sequence helps to ensure thorough inputting of programable parameters for the medical device. One aspect of the system is to provide a navigational sequence to ensure thorough programming of parameters for an implantable cardiac rhythm management device. Another aspect of the present system is to divide the entire set of programmable parameters into a plurality of subsets. Each individual subset of programmable parameters is presented to the medical personnel at a time. The present system further provides navigational links to assist the medical personnel in proceeding to a next interface that presents the medical personnel with a different subset of programmable parameters to input. In an embodiment, the subsets are broken down so that inputs on the displayed interface are related to an operation of the cardiac rhythm management device.

Another embodiment of the present system is a medical system including a medical device and a programmer for the medical device.

Another embodiment is a method for programming parameters of a medical device including displaying a start interface, querying the user to start programming at least one parameter into a profile, displaying a first of a plurality of sequentially linked parameter programming interfaces, providing a back navigation button on a displayed parameter programming interface, and providing a next navigation button on a displayed parameter programming interface. Each of the parameter programming interfaces include at least one parameter input field.

Other aspects of the system will be apparent on reading the following detailed description of the system and viewing the drawings that form a part thereof.

BRIEF DESCRIPTION OF THE DRAWINGS

FIGS. 5A–5D are views illustrating a navigational interface according to an embodiment of the present system.

FIGS. 6A–6F are views illustrating a further navigational interface according to an embodiment of the present system.

FIGS. 7A–7F are views illustrating a further navigational interface according to an embodiment of the present system.

FIGS. 9A–9D are views illustrating a further navigational interface according to an embodiment of the present system.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents.

The present method and apparatus will be described in embodiments involving implantable medical devices including, but not limited to, implantable cardiac rhythm management systems such as pacemakers, cardioverter/ defibrillators, pacer/defibrillators, and biventricular or other multi-site coordination devices. However, it is understood that the present methods and apparatus may be employed in unimplanted devices, including, but not limited to, external pacemakers, cardioverter/defibrillators, pacer/defibrillators, biventricular or other multi-site coordination devices, monitors, programmers and recorders.

The description herein uses the term "button" to describe a computer selection device which will cause a result when activated. For example, software may display a button on a screen. The button is "clicked" on by a mouse, pointer, or other selection device to activate the button and cause the software to perform a function, for example store the inputs on the current interface in memory and move to a different interface. Activation of a button can also occur through the use of keyboard commands, such as tab commands and enter commands as are conventional. Further, a button includes icons and other indicia indicating the status as a device which causes a particular result when activated. For example, a button that forces the software to move to a next interface in a sequence of interfaces may be labeled as "next" or "continue".

Figure 1:
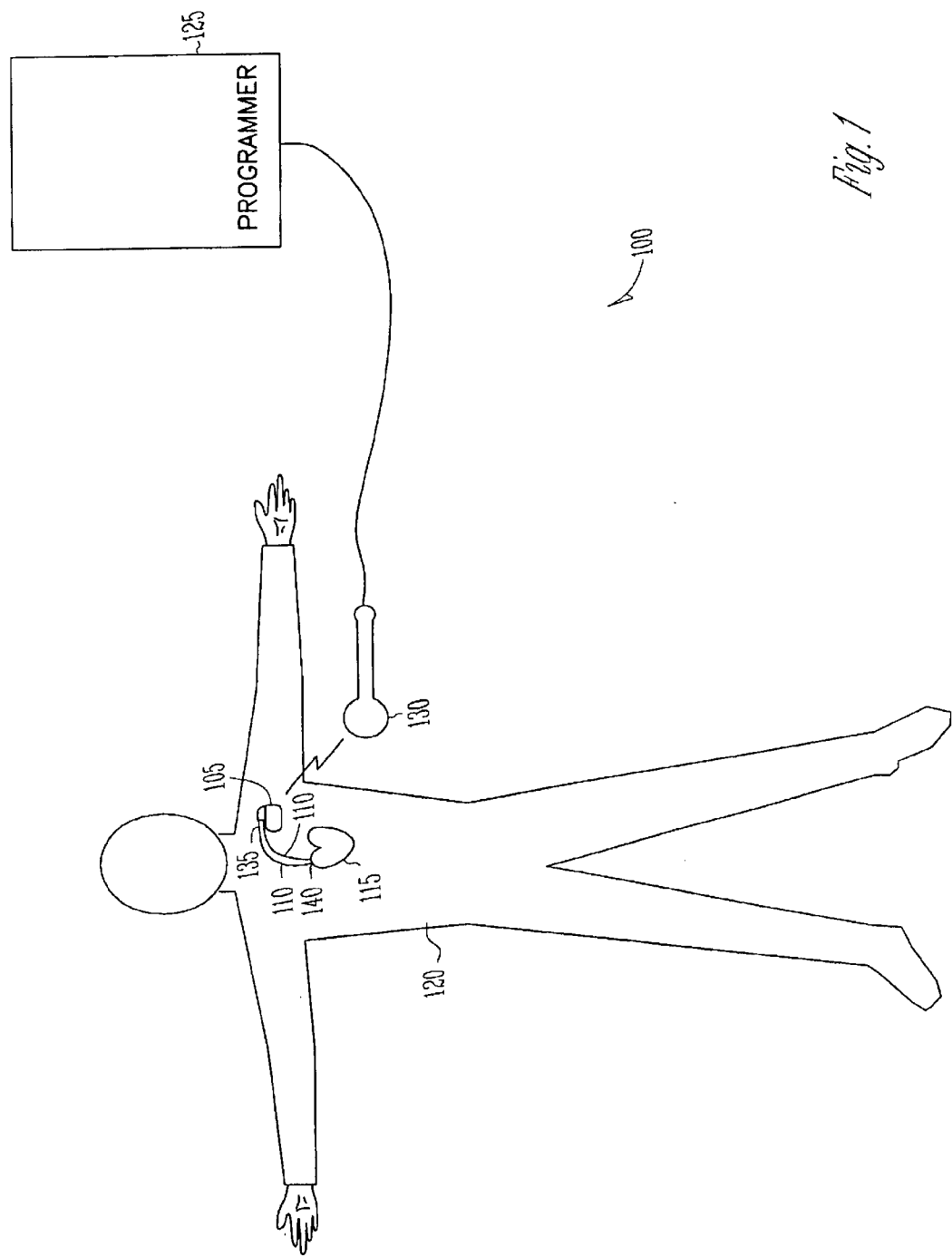
FIG. 1 is a view illustrating generally one embodiment of portions of a cardiac rhythm management system and an environment in which it is used.

FIG. 1 is a schematic illustration of one embodiment a cardiac rhythm management system 100 and an environment in which it is used. System 100 includes an implantable cardiac rhythm management ("CRM") device 105 coupled by an intravascular endocardial lead 110, or other lead, to a heart 115 of patient 120. Catheter lead 110 includes a proximal end 135, which is coupled to device 105, and a distal end 140, which is coupled to one or more portions of heart 115. CRM device 105 contains electronic circuitry adapted to perform various tasks associated with cardiac rhythm management. CRM device 105 includes processing circuits and memory for storing instructions for at least one therapy, a profile of programmable parameters associated with the at least one therapy, and measured patient cardiac data. The processing circuits perform cardiac rhythm management therapy based on the programmed parameters and, in some cases, measured patient cardiac data. Examples of CRM devices include the VENTAK®, PULSAR™, DISCOVERY™, MERIDAN™ and VIGOR™ families of implantable cardioverter defibrillators, automatic implantable cardioverter defibrillators, pacing systems and pacemakers, all by Cardiac Pacemaker, Inc. of St. Paul, Minn. System 100 also includes an external medical device programmer 125 providing wireless communication with device 105 using a communication device 130.

Figure 2:
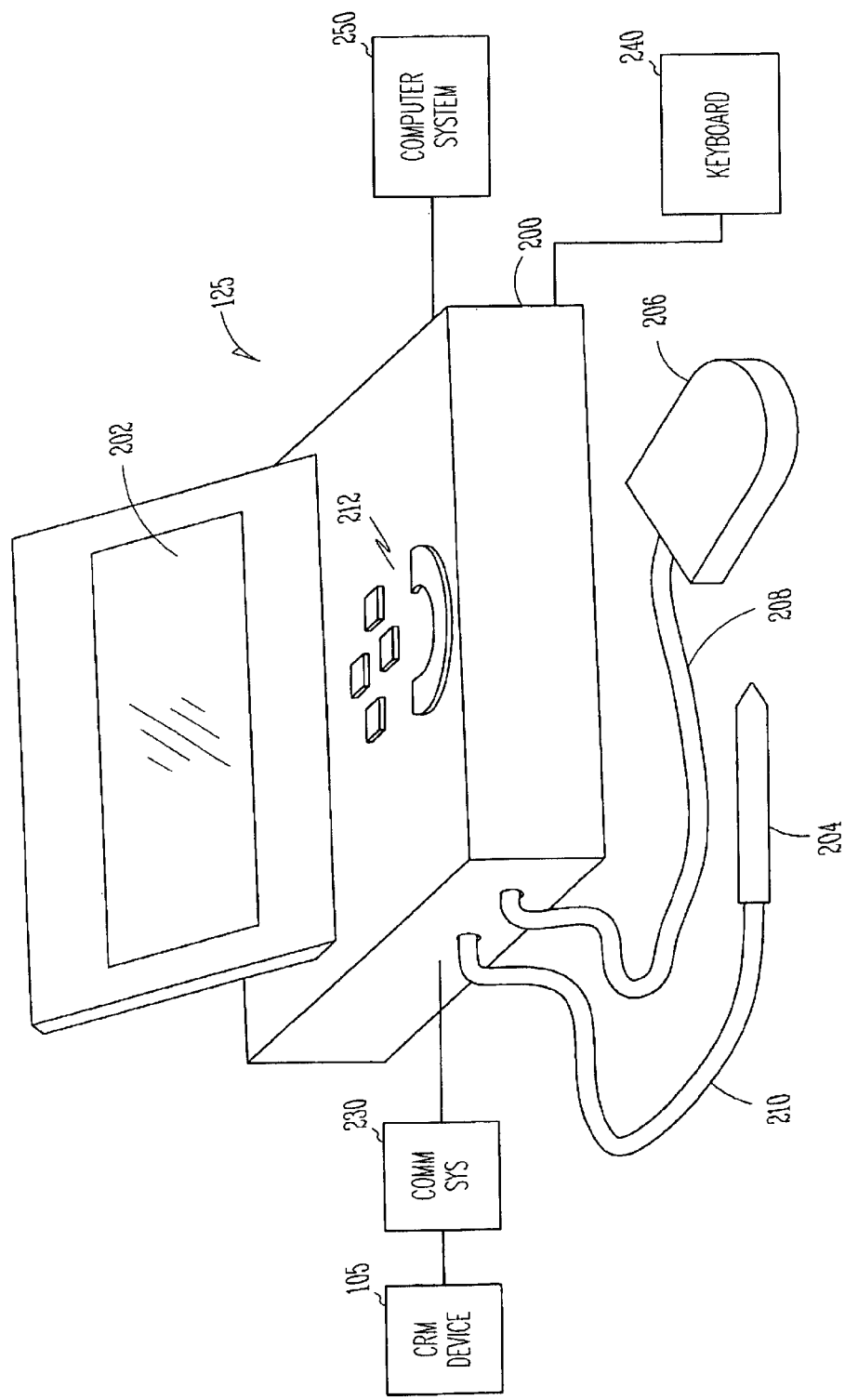
FIG. 2 is a view illustrating a programming system according to an embodiment of the present system.

FIG. 2 shows one embodiment of a medical device programmer 125 of the medical device system. An example of a medical device programmer is the ZOOM™ programming system by Cardiac Pacemaker, Inc. of St. Paul, Minn. As previously mentioned, one embodiment of the medical device programmer 125 for the implantable CRM device 105 takes the form of an external controller. However, in an alternative embodiment, the medical device system is a completely external device such as an external cardioverting/defibrillator system as are known in the art, where the programmer unit is physically and electronically integrated into electronic control circuitry. In an embodiment, the electronic control circuitry of the external cardioverting/defibrillator system performs the same functions as the implantable CRM device 105 described herein. In an embodiment, the electronic control circuitry of the external cardioverting/defibrillator system is the same as the electronic control circuitry of CRM device 105. An example of this latter embodiment is for an external cardiac monitor and defibrillation unit, electrically connected to the heart by any combination of intracardiac catheters, epicardial electrodes and/or external cardiac electrodes.

Medical device programmer 125 is designed to be positioned external of the human body 120 for communicating with an implantable medical device, such as CRM device 105 in FIG. 1, for example via wireless communication, RF telemetry or signal induction. Medical device programmer 125 has programmer electronic circuitry, including a microprocessor and related circuitry, such as digital memory, which is coupled to an output unit, which is here shown as display screen 202.

In one embodiment, the medical device programmer 125 has an outer housing 200 which is made of metal alloy, a thermal plastic or other suitable lightweight durable material. The display screen 202 is disposed on the upper surface of housing 200. The display screen 202 folds down into a closed position when medical device programmer 125 is not in use, thereby reducing the size of medical device programmer 125 and protecting the display surface of display screen 202 during transportation and storage. In another embodiment, the display screen 202 is fixed in a single position, for example fixed directly on the housing. An embodiment of the present system includes providing the programmer 125 with a video output connection to which a non-integral monitor can be connected. The interfaces as described herein may then be displayed on the non-integral monitors. In some embodiments, the external programmer additionally has a non-volatile storage, such as machine readable media, floppy disks, internal memory (e.g. BIOS, ROM) and a hard drive, and volatile storage, such as internal memory (e.g. RAM) disposed within the housing.

The medical device programmer 125 is shown with the display screen 202 positioned in one of a plurality of possible open positions such that a display on the display screen 202 is visible to a user situated in front of medical device programmer 125. In one embodiment, the display screen 202 is of a CRT, LCD or electroluminescent type. The display screen 202 is operatively coupled to the electronic circuitry disposed with the housing 200 and is adapted to provide a visual display of graphics and/or data under control of the programmer electronic circuitry, e.g. processor and memory. The processor may be a commercially available processor available from Intel®, Cyrix®, AMD™ or other manufacturers, or may be a dedicated processor specifically designed for a medical device programmer. The processor runs either a commercially available operating systems or specially designed operating systems dedicated to medical device programmers. The memory in the programmer stores software for programming parameters into a profile of parameters for a therapy. The memory further stores programmable parameters that are used by the software to control operation of the CRM device.

Medical device programmer 125 further includes a user input device coupled to the electronic circuitry. In one embodiment, the user input device is the screen 202, which is provided with touch-sensitive capability, such that a user can interact with the programmer electronic circuitry by touching the display area on screen 202 with a finger (not shown), a stylus 204, or other pointing device. In one embodiment, the touch-sensitive display screen is the primary input for the medical device programmer 125. The medical device programmer 125 further includes a programming head 206, which is place over a patient's body near the implant site of an implanted device, such as CRM device 105, in order to establish a communication link between CRM device 105 and programmer 125. The communication link between CRM device 105 and programmer 125 allows the electronic circuitry of programmer 125 to be coupled to the electronic control circuitry of the CRM device 105. The programming head 206 is coupled to the electronic circuitry of medical device programmer 125 by a cable 208 and includes a receiver circuit for receiving signals from a transmitter circuit of CRM device 105. In another embodiment, a communication system 230 is intermediate programmer 125 and the CRM device 105, for example the telephone system or a computer network such as a LAN, WAN, or global computer network (e.g. internet). Consequently, the programmer 125 remotely monitors and receives data from the CRM device 105. In one embodiment, communication system 230 establishes a type of client/server relationship between the CRM device 105 and the programmer 125.

In one embodiment of the system, stylus 204 used to interact with the touch-sensitive display screen 202 is coupled to the programmer electronic circuitry within the housing 200 by a cable 210. In another embodiment of the system, only a touch sensitive screen 202 is provided which is activated by a user's finger touching the screen. Alternatively, medical device programmer 125 may be equipped with a conventional computer "mouse"-type pointing device, rather than a stylus or a touch sensitive screen which is actuatable by a user's finger. In the absence of either a stylus, touch-sensitive screen or a mouse, on-screen cursor control for enabling user interaction with medical device programmer 125 may be facilitated through cursor control keys 212 (arrow keys or the like) disposed on medical device programmer 125. Another embodiment in lieu of the touch sensitive screen, mouse, or stylus, is providing a serial connection on the programmer 125 for using a keyboard 240 as the input device.

Programmer 200 is also connectable to a computer system 250, for example direct connection through parallel ports or universal bus, modems over telephone connections, LAN, WAN, or other global computer network connections, all represented at 252 in FIG. 2. While the description herein focuses on the programmer 125 providing the navigation and guidance for setting up profiles of parameters for CRM device 105, it will be understood that it is within the scope of the present system to perform the navigation and guidance for programming parameter profiles in computer system 250 separate from programmer 200. Thereafter, the profiles are download to the programmer 200, for example over connection 252 or by downloading the profile to a portable data storage medium and loading the profile from the medium to the programmer 125 for subsequent programming of CRM device 105.

Figure 3:
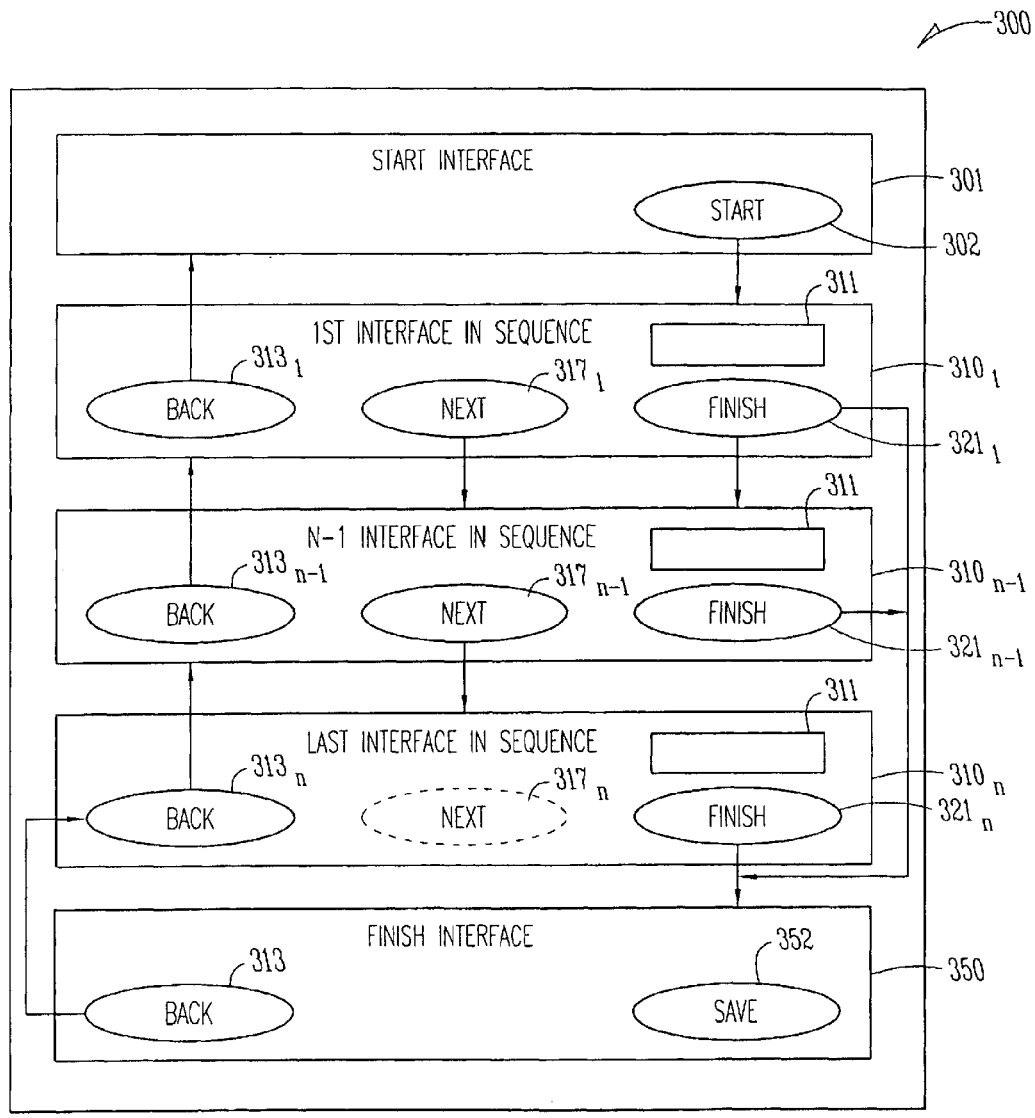
FIG. 3 is a flowchart of a navigational sequence according to an embodiment of the present system.

FIG. 3 shows a flowchart of a navigational and guidance sequence of programming interfaces 300 which are linked together for ease of navigation and programming. The interfaces of the navigational and guidance sequence are graphical user interfaces (GUI's) that are displayed on screens 202 or computer system 250. The navigational sequence 300 includes a start interface 301, at least one parameter programming interface 310, and a finish interface 350. The start interface 301 includes directions and links allowing the user to select from various movement functions in the navigational and guidance sequence. Start interface 301 has a start button 302 that links the start interface to a first parameter programming interface $310_1$. A user activates start button 302, for example by touching a touch sensitive display 202 at the start button or clicking on the start button with a pointing device, such as a mouse or stylus, or by other equivalent action. It is also within the scope of the present system to use keyboard command, such as tab or arrow keys to cycle through various buttons on the start interface 301 until the start button is selected and depressing the enter key will activate start button 302. In the present description, the term "activate" and its derivatives are used to define activation of a link which causes the programmer or computer to perform an action in its program for creating parameter profiles. Activating start button 302 initiates a step in the navigation sequence and causes the navigational sequence to proceed to the first parameter programming interface $310_1$.

All programming interfaces 310 include at least one programming parameter input field 311 for inputting a programmable parameter for use in a CRM implant device and buttons for navigating the sequence of programming interfaces 300. As shown in FIG. 3, the programming interfaces 310 include "n" programming interfaces 310, where "n" is the number of interfaces. Programming interfaces $310_1$–$310_n$ each include a back button 313, which upon activation returns the navigational sequence to the previous interface. In the case of interface $310_1$, activating back button $313_1$ causes the navigational sequence to return to start interface 301. In the case of interface $310_n$ activating back button $313_n$ causes the navigational sequence to move back to interface $310_{n-1}$. Programming interfaces $310_1$–$310_{n-1}$ each include a next button 317, which upon activation forwards the navigational sequence to the subsequent interface. In the case of interface $310_1$, activating next button $313_1$ causes the navigational sequence to proceed to the programming interface $310_2$ (not shown). In the case of interface $310_{n-1}$, activating next button $313_{n-1}$ causes the navigational sequence to proceed to interface $310_n$. The last programming interface $310_n$, unlike programming interfaces $310_1$–$313_{n-1}$, does not have a next button which can be activated. In one embodiment, the next button $317_n$ is displayed; however, it is "greyed" out. The "greying" out of next button $317_n$ is indicated by dashed line in FIG. 3. As is conventional in computer systems, "greying" out a button indicates that it is inactive and may not be activated by the user. Programming interfaces $310_1$–$310_n$ each include a finish button $321_1$–$321_n$, which upon activation, the navigational sequence bypasses any subsequent programming interface and moves directly to finish interface 350.

Finish interface 350 includes a back button 313, which upon activation will return the navigational sequence to previous programming interface $310_n$. Finish interface 350 further includes a save button 352, which upon activation will save the parameters entered into all input fields 311 of programming interfaces $310_1$–$310_n$ as a profile.

In an embodiment of the present invention relating to the programming of cardiac rhythm management devices, the number of interfaces, $310_1$, $310_2$ and $310_3$ is three. A first interface $310_1$ provides the medical personnel with input fields for device parameters relating to tachycardia. The first interface $310_1$ includes a plurality of links to sub-interfaces that each include a subset of device parameters relating to tachycardia. These tachycardia sub-interfaces, in an embodiment, return to the first interface $310_1$ prior to the programming sequence moving on to the second interface $310_2$. In another embodiment, the tachycardia sub-interfaces are linked together to cause the programming sequence to step through more than one tachycardia sub-interface prior to returning to the first interface $310_1$. The second interface $310_2$ includes a plurality of links to sub-interfaces that each include a subset of device parameters relating to bradycardia. These bradycardia sub-interfaces, in an embodiment, return to the second interface $310_2$ prior to the programming sequence moving on to the end interface 350. In another embodiment, the bradycardia sub-interfaces are linked together to cause the programming sequence to step through more than one bradycardia sub-interface prior to returning to the second interface $310_2$. A third interface $310_3$ includes a plurality of links to custom parameter sub-interfaces that each include a sub-set of custom parameter input fields. The custom parameter input fields relate custom parameters for the medical therapy device that are used to control custom features of the medical device. Examples of custom features include magnet operation control, sound control, patient triggered operation control, trending analysis control, sensitivity adjustment control, data measurement control, and therapy feature control.

Figure 4:
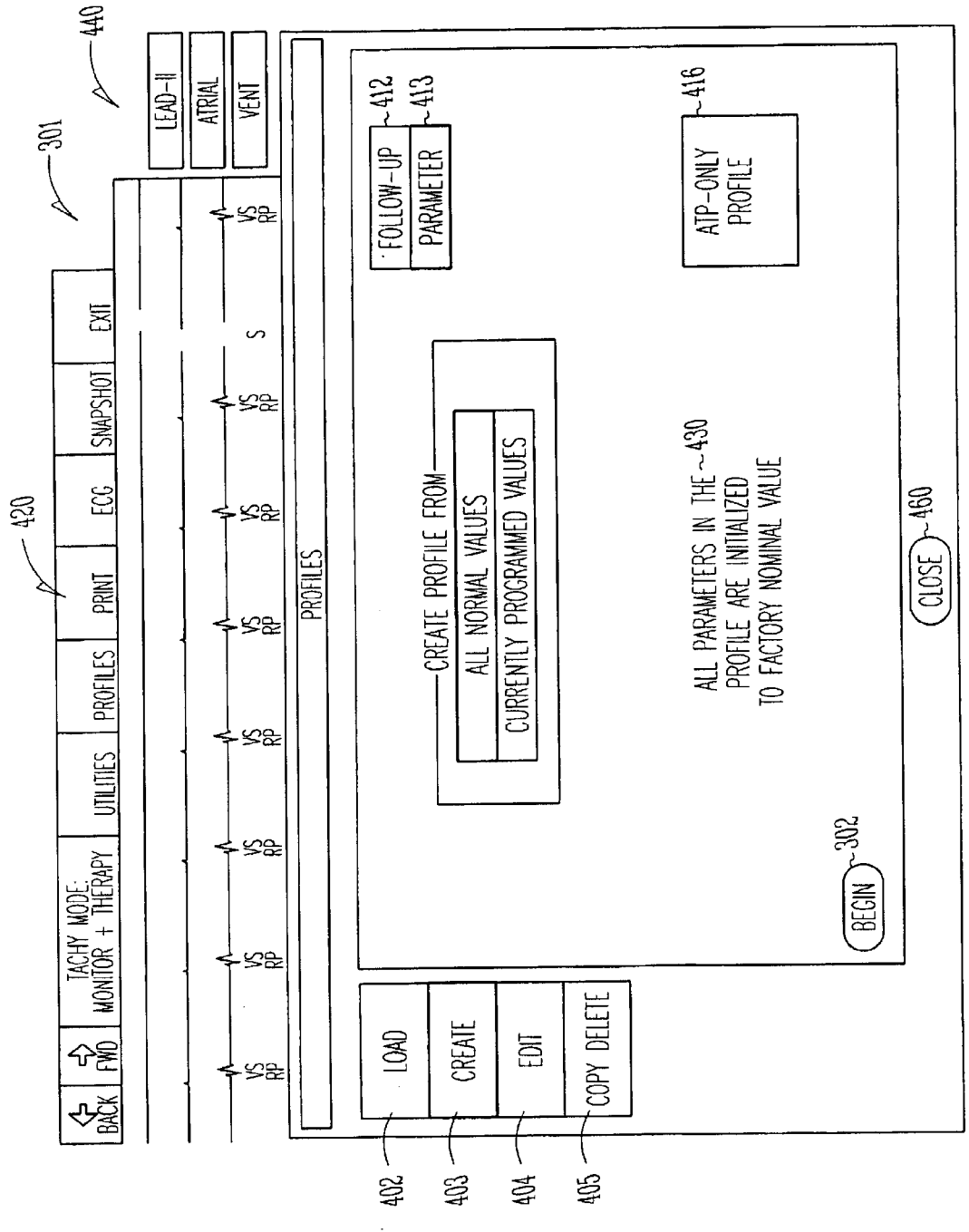
FIG. 4 is a view illustrating a start interface according to an embodiment of the present system.

A more detailed embodiment of the navigational sequence used to program a parameter profile for CRM device 105 will now be explained in conjunction with FIGS. 4–8. FIG. 4 illustrates start interface 301 shown on display 202. Start interface 301 includes a plurality of different buttons 402, 403, 404, 405. The load button 402, when activated, navigates the user to an interface that prompts the user for inputs, such as file name and path, to load a previously created parameter profile. The create button 403 shown as selected which will navigate the user to a first interface $310_1$. The edit button 404, when activated, navigates the user to an interface that allows the user to modify a parameter profile. The copy/delete button 405, when activated, navigates the user to an interface that allows the user to copy a stored parameter profile or delete a stored parameter profile. Start interface 301 further includes a follow-up button 412 and a parameter button 413. The follow-up button 412 navigates the user through a sequence of follow-up interfaces. An embodiment of a follow-up profile programming sequence is described below with reference to FIGS. 9A–9D. The parameter button 412 navigates the user through a sequence of parameter programming interfaces. Start interface 301 further includes a plurality of function buttons 420 at the top of the interface. Each of these buttons 420 performs a specified function as indicated thereon. Start interface 301 also includes an information field 430 which displays information related to the selected buttons. FIG. 4 shows information in information field 430 related to the follow-up function and the create parameter profile function. Interface 301 includes a close button 460 and start or begin button 302. If the user activates the close button 460, then the program ends. If the user activates the begin button 302, then the sequence for inputting parameters to create a profile starts. The follow-up profile button 412, when activated along with start button 302, navigates the user to a follow-up profile routine. The follow-up programmer routine is the use of the programmer to interact, e.g., interrogate and acquire data from a previously programmed medical therapy device or modify the parameters stored in the medical therapy device. One example of when the follow-up function is used is a patient's routine follow-up visits to the doctor. A similar sequence of interfaces as described herein are used in such a follow-up function. The follow-up routine generally provides the user with prompts for inputting follow-up parameters on therapy provided by an implant that is already in use. For example, the follow-up routine prompts tests to be performed on the CRM device, checks parameters stored in the CRM device, prompts reports to be produced by the programmer with data from the CRM device, prompts the user for notes and/or events related to the CRM device.

It will be understood that the present invention is adaptable to other programming functions of a programmer for a medical therapy device, such as a cardiac rhythm management device. One example of another programming function is antitachycardia pacing parameter (ATP) programming. Activation of the ATP-only button 416 navigates the user to ATP programming related interfaces. A similar sequence of interfaces as described herein are used in such an ATP programming function. In another embodiment, the ATP-only 416 button may be on a programming interface for example on the interface $310_1$.

Interface 301 also includes a waveform display 440 that displays various waveforms and data related to the therapy. Display 440 is configurable to show realtime data received from the medical device or stored data from either the medical device or data in the programmer. The display 440 is adapted to show a waveform associated with one of the two leads 110, a sensed atrial waveform, a sensed ventricular waveform, and event markers. The event markers include ventricular sensing, ventricular pacing, ventricular events during the refractory period, atrial-paced events.

FIGS. 5A through 5D show a further interface 502 in the navigational programming sequence. Interface 502 is also displayed on screen 202. Interface 502 is a base Tachy interface for programming a set of Tachy-related parameter input fields. Interface 502 upon selection of certain control buttons displays different sub-set of Tachy relate parameter input fields, i.e., sub-interfaces. Interface 502 includes display section 505 in which are displayed directions that direct the user how to input CRM device programmable parameters and navigate the interfaces of the navigational sequence. In the illustrated embodiment, direction section 505 explains how to enter programmable parameter values for a custom implantable medical device profile and how to navigate the sequence of interfaces and sub-interfaces. The sub-interfaces are the interface 502 with different parameter input fields displayed. This embodiment indicates that the present profile for implantable device is for a DDD setting of a cardiac rhythm management device as indicated at 510. While the illustrated embodiment indicates a DDD setting, it will be understood that other CRM device settings are also used with the teachings according to the present system. Other CRM device settings include, but are not limited to, DDDR, DDIR, DDI, VDD, VVIR, VVI, AAIR, AAI, OOOR, and an off setting. Still other CRM device settings include AAO, AOO, AAT, AATR, AOOR, DDDRD, DDT, DOO, DVI, DVIR, SSI, SSIR, VAT, VOO, VOOR, VVICD, VVT, and VVTR. Other embodiments of CRM device settings are known to those of in the art. Additional data relating to the CRM device setting is also shown at 510, e.g., the pacing per minute data associated with the DDD setting. Interface 502 further includes zone selection buttons 512, which when selected by the user indicate the number of rate zones for the DDD pacing, here shown as 1, 2, or 3 as represented by separate selectable buttons. The zone button corresponding to two zones is selected in the embodiment shown in FIGS. 5A–5D. Accordingly, two zone settings (VT, VF) are displayed at 516 to the right of the zone selection buttons 512. The zone settings 516 indicate the beats per minute thresholds dividing the two zones and the particular CRM device settings corresponding to each of the parameter settings for the two zones. The settings include stroke volume index. The settings include a sustained-rate duration indicator that shows the time period for sustained rate duration. Sustained rate duration allows delivery of therapy if an arrhythmia has exceeded the programmed elapsed time, regardless of sudden onset of a stability criteria. In addition, when an arrhythmia occurs at an "extended high rate" interval, the device can be programmed to provide shock therapy. The settings also include the energy associated with the ATP (antitachycardia pacing). It is within the scope of the present system to provide other data, buttons, etc. as appropriate for other CRM device settings in place of zone selection buttons and zone settings 516. With only a single zone selected at 512, then one of the VT and VF button fields at 516 is displayed. With all three zones selected at 512, then a VT-1, VT and VF button fields are displayed at 516.

Various programable parameter input fields are shown at 518 for DDD programming a profile for the CRM device are shown below the setting 510, zone selection buttons 512 and zone settings 516. The shown parameter input fields are associated with the selected button in the VT area of zone settings 516. Programmable parameter initial input fields for the current profile include rate 521, interval 522, duration 523, and Rhythm ID SVT inhibitor 526. Programmable parameter redetection profile input fields for the current selected VT button include redetection duration 531 and post-shock duration 532. The input fields 521–523, 526, 531–532 are a sub-set of the set of parameters relating to Tachy parameters that are programmable into a profile. It will be appreciated by one of ordinary skill upon reading the present disclosure that other programmable parameter inputs would be provided for other settings for a CRM device. That is, the present system is not limited to only programming parameters for a DDD setting of the CRM device. It is within the scope of the present system to provide other input fields as appropriate for other CRM device settings in place of DDD input fields 521–523, 526, 531–532.

The interface 502 also includes the cancel button 450, the back button 313, the next button 317, and the finish button 321 as described herein. The back button 313, upon its activation, will return the navigational sequence of the illustrated embodiment to the prior, start interface 301 shown in FIG. 4. The next button 317, upon its activation, forwards the navigational sequence of the illustrated embodiment to a next programming interface 602 as shown in FIGS. 6A–6F. The finish button 321, upon its activation, forwards the navigational sequence of the illustrated embodiment to an end interface 802 as shown in FIG. 8. As a result, the user must follow a set navigational sequence through the programming interfaces for creating or editing a parameter profile. For example, the user can only move to interfaces 301, 602, and 802 from interface 502. That is, the user can not jump directly to a non-linked interface, e.g. interface 702 of FIG. 7, from interface 502.

Figure 5A:
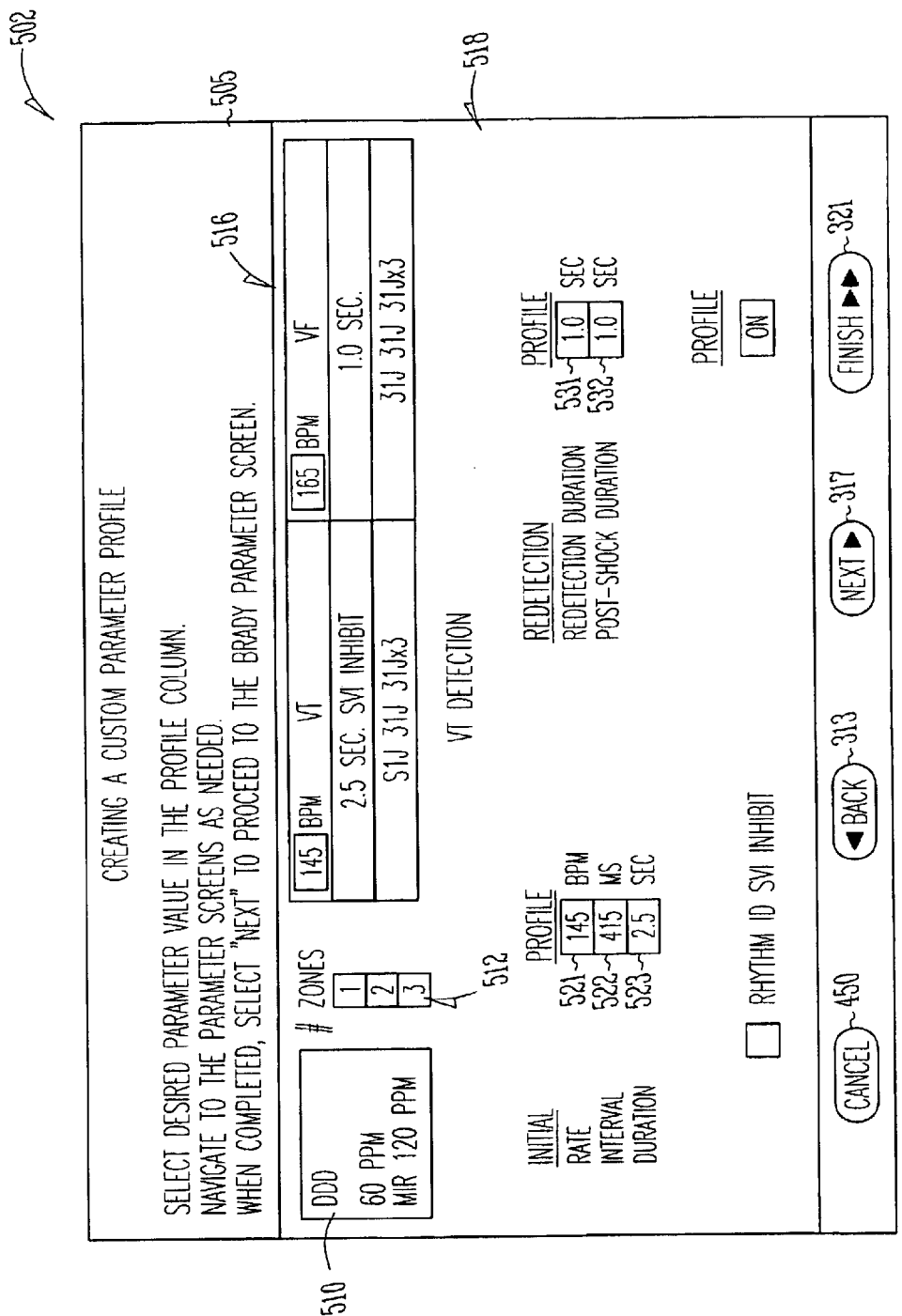

FIG. 5B shows the an interface similar to FIG. 5A expect that the input fields at 518 have changed to allow programming of a different sub-set of Tachy related parameters. The FIG. 5A interface and the FIG. 5B interface are both sub-interfaces of the tachy parameter input interface for creating a profile. The FIG. 5B input fields are associated with the lower button of the VT field. The first antitachycardia pacing (ATP) ATP1 is on and set in a burst mode. Accordingly, the input fields for ATP are displayed to the user. The second ATP, ATP2, is off. Accordingly, the input fields associated with ATP2 are not displayed. If ATP2 was on, then input fields for ATP2 are displayed. The input fields for ATP are number of bursts field 541, pulses per burst initial field 542, pulses per burst increment field 543, pulses per burst maximum (not shown), coupling interval field 545, coupling interval decrement (not shown), burst cycle length 547, burst cycle length ramp decrement 548, burst cycle scan decrement (not shown), and a minimum interval field 549. The energy for each shock under the VT application of DDD is programmed at input fields 551, 552. An ATP time out input field is provided at 555.

FIG. 5C shows the an interface similar to FIG. 5A expect that the input fields at 518 have changed to allow programming of a different sub-set of Tachy related parameters. These input fields are associated with the upper button of the VF field. Programmable parameter inputs for the current profile include rate 521, interval 522, and duration 523.

FIG. 5D shows the an interface similar to FIG. 5A expect that the input fields at 518 have changed to allow programming of a different sub-set of Tachy related parameters. These input fields are associated with the lower button of the VF field. Programmable parameter inputs for the current profile include an energy value for a first shock 531, and energy value for a second shock 532, and the number of additional shocks 561. If the number of additional shocks input into field 561 is greater than zero, then additional energy input fields are shown in area 518.

An embodiment of the navigation sequence of the present invention proceeds to interface 602 upon activation of the next button 317 in any of the interfaces shown in FIGS. 5A to 5D. Activation of the back button 313 in any of the interfaces shown in FIGS. 5A to 5D returns the user to the start interface 301 shown in FIG. 4. Activation of the finish button 321 in any if the interfaces shown in FIGS. 5A to 5D moves the sequence directly to finish interface 802.

FIGS. 6A–6F show a further programming interface 602 in the navigational programming sequence. Each of FIGS. 6A–6F show a differnt sub-interface of brady programming interface 602. Interface 602 is displayed on screen 202 and includes a direction section 605 in which are displayed directions that direct the user how to input CRM device programmable parameters and navigate the interface in the navigational sequence. In the illustrated embodiment, direction section 605 explains how to enter programmable parameter values for a custom implantable medical device profile and how to navigate the sequence of interface.

Interface 602 shows the type of CRM device setting at 612, here DDDR, and the current setting for the post-shock at 613, here DDD, as shown in FIGS. 6A–6F. A plurality of input fields are shown in area 614 of interface 602. These inputs fields are associated with the button 612 and are displayed when button 612 is selected. The input fields at 614 include a mode input field, an Antitachy response input field, lower rate limit input field, maximum tracking rate input field, maximum sensor rate input field, AV delay (paced) input field (not shown), atrial pulse width input field, atrial amplitude input field, atrial refractory (PVARP) input field (not shown), ventricular pulse width input field, ventricular amplitude input field, ventricular refractory input field (not shown), and post-shock delay input field. These input fields 614 are a sub-set of all Brady related programmable parameters.

Interface 602 includes, on the right side of each of FIGS. 6A–F, a further sub-set of brady related input fields at 618. A plurality of buttons for selecting additional programming profile input fields is positioned at area 618. These buttons include a sensor button 621, a tachy response button 623, a rate enhancement button 625, an AV delay button 627, a refractory button 629, and a noise response button 631. The user selects one of these buttons and input fields associated with the selected button are displayed on interface 602. The sensor button 621 is selected in FIG. 6A; the interface 602 shows the input fields associated with the sensor features of the CRM device in a DDDR mode. Accordingly, the accelerometer input fields of activity threshold, reaction time, response factor and recovery time are shown and available for programming the profile or parameters. These input fields represent a sub-set of programmable parameters for the brady mode of a CRM device.

Figure 6A:
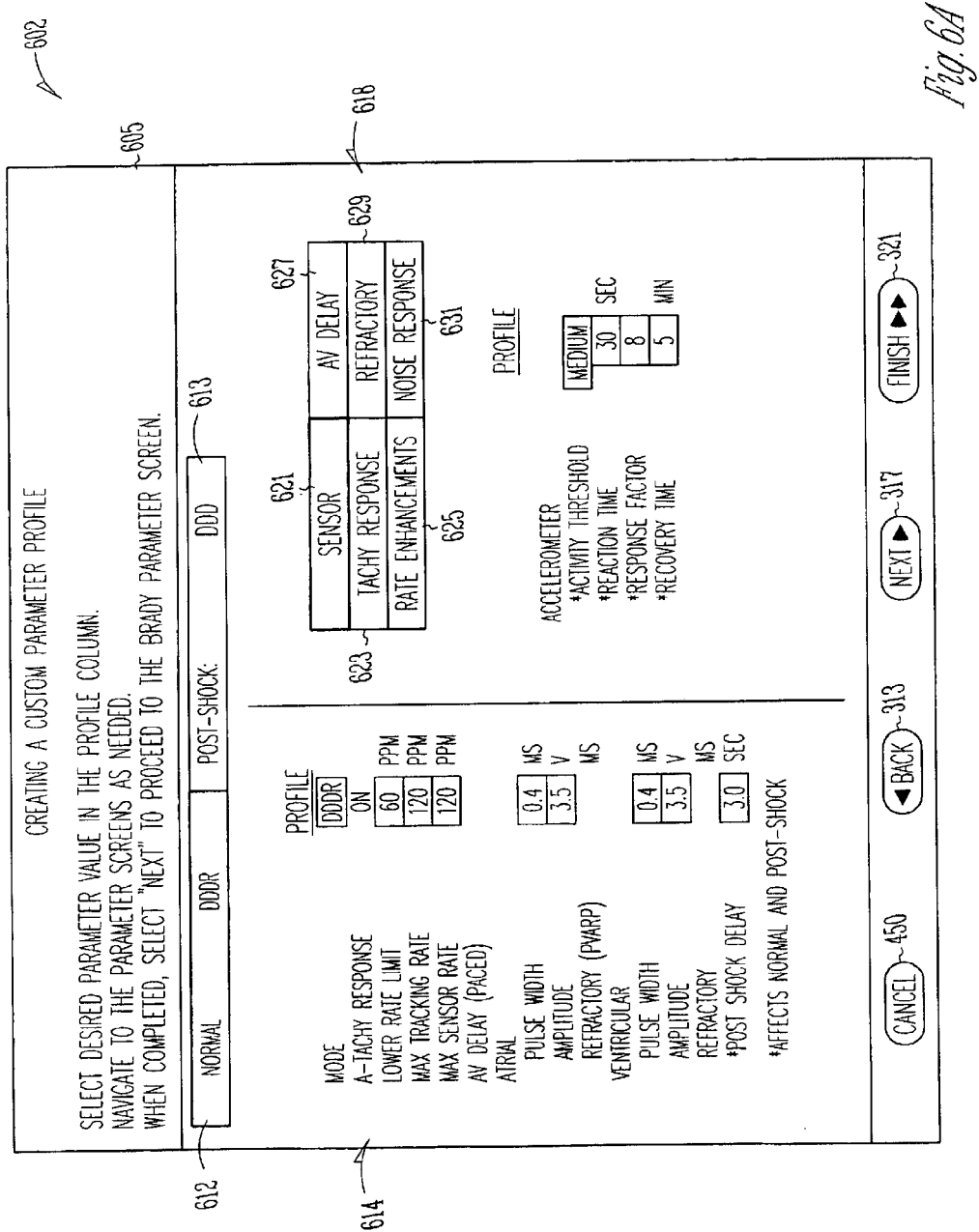
Figure 6B:

FIG. 6B shows the input fields in area 618 of interface 602 when the Tachy response button 623 is selected. The input fields associated with the Tachy response button 623 include trigger rate, duration, entry count, exit count, fallback mode, fallback time, ATR/VTR fall back LRL, atrial flutter response, PMT termination, ventricular rate regulation, and maximum pacing rate. These input fields represent a sub-set of programmable parameters for the brady mode of a CRM device.

FIG. 6C shows the input fields in area 618 of interface 602 when the rate enhancement button 625 is selected. The input fields associated with the rate enhancement button 625 include rate hysteresis, rate hysteresis offset, search hysteresis, rate smoothing, rate smoothing up, rate smoothing down, rate smoothing maximum pacing rate, atrial pacing preference, maximum atrial pacing rate, and atrial pacing search interval. These input fields represent a sub-set of programmable parameters for the brady mode of a CRM device.

FIG. 6D shows the input fields in area 618 of interface 602 when the AV delay button 627 is selected. The input fields associated with the AV delay button 627 include dynamic AV delay, maximum delay, minimum delay, sensed AV offset, AV search hysteresis, AV hysteresis search interval, AV search hysteresis AV increase. These input fields represent a sub-set of programmable parameters for the brady mode of a CRM device.

FIG. 6E shows the input fields in area 618 of interface 602 when the refractory button 629 is selected. The input fields associated with the refractory button 629 include dynamic PVARP, maximum PVARP, minimum PVARP, PVARP after PVC, dynamic VRP, maximum VRP, minimum VRP, V-blank after A-pace, A-blank after, V-pave, and A-blank after V-sense. These input fields represent a sub-set of programmable parameters for the brady mode of a CRM device.

FIG. 6F shows the input fields in area 618 of interface 602 when the noise response button 631 is selected. The input fields associated with the noise response button 631 include a noise response input field. This input field represents a sub-set of programmable parameters for the brady mode of a CRM device.

The post-shock parameters in a brady mode are also divided into a plurality of sub-sets. When the post-shock button 613 is selected, then the post-shock related input fields are displayed. In an embodiment, the post-shock inputs fields are divided into sub-sets that are the same as those shown in area 618 in FIGS. 6A–6F and described herein.

The interface 602 also includes the cancel button 450, the back button 313, the next button 317, and the finish button 321 as described herein. The back button 313, upon its activation, will return the navigational sequence of the illustrated embodiment to prior interface 502. The next button 317, upon its activation, forwards the navigational sequence of the illustrated embodiment to the next interface 702 as shown in FIGS. 7A–7F. The finish button 321, upon its activation, forwards the navigational sequence of the illustrated embodiment to the end interface 802 as shown in FIG. 8. As a result, the user must follow a predetermined navigational sequence through the programming interfaces for a select programming setting. For example, the user can only move to the interfaces 502, 702, and 802 from interface 602. The navigational sequence will not allow the user to jump directly to interface 301 from interface 602.

FIGS. 7A–7F show a further programming interface 702 in the navigational sequence. The interface 702 is displayed on screen 202. Interface 702 includes a direction section 705 in which are displayed directions that direct the user how to input CRM device programmable parameters and navigate the interface. In the illustrated embodiments, direction section 705 explains how to enter programmable parameter values for a custom implantable medical device profile and how to navigate the sequence of interfaces.

Interface 702 shows a plurality of selection buttons 711–714, 716–718 displayed in a column 719 shown on the left side of FIGS. 7A–7F. In the illustrated embodiment, the column 719 of buttons includes magnet/beeper button 711, episodes/EGM button 712, patient triggered events button 713, trending button 714, sensitivity adjustment button 716, daily measurement button 717, and therapy features 718 button. Only one of buttons 711–714, 716–718 is selected at any one time. The selection of one button causes parameter profile input fields to be displayed on the interface 702. Each selection button 711–714, 716–718 has certain programmable parameter input fields associated with the respective button. The associated input fields are displayed when the respective button is activated in area 720 of interface 702.

Figure 7A:
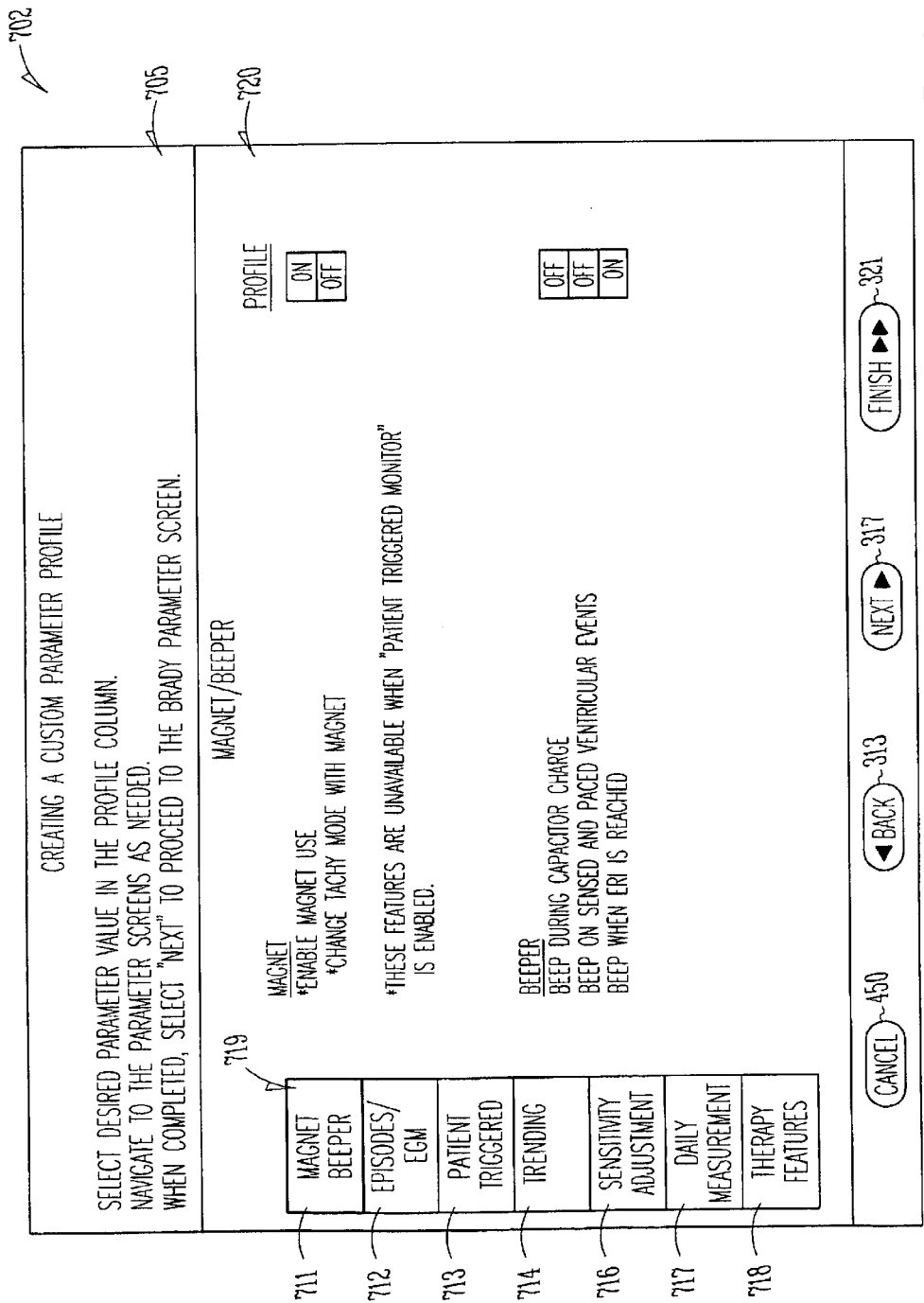
Figure 8:
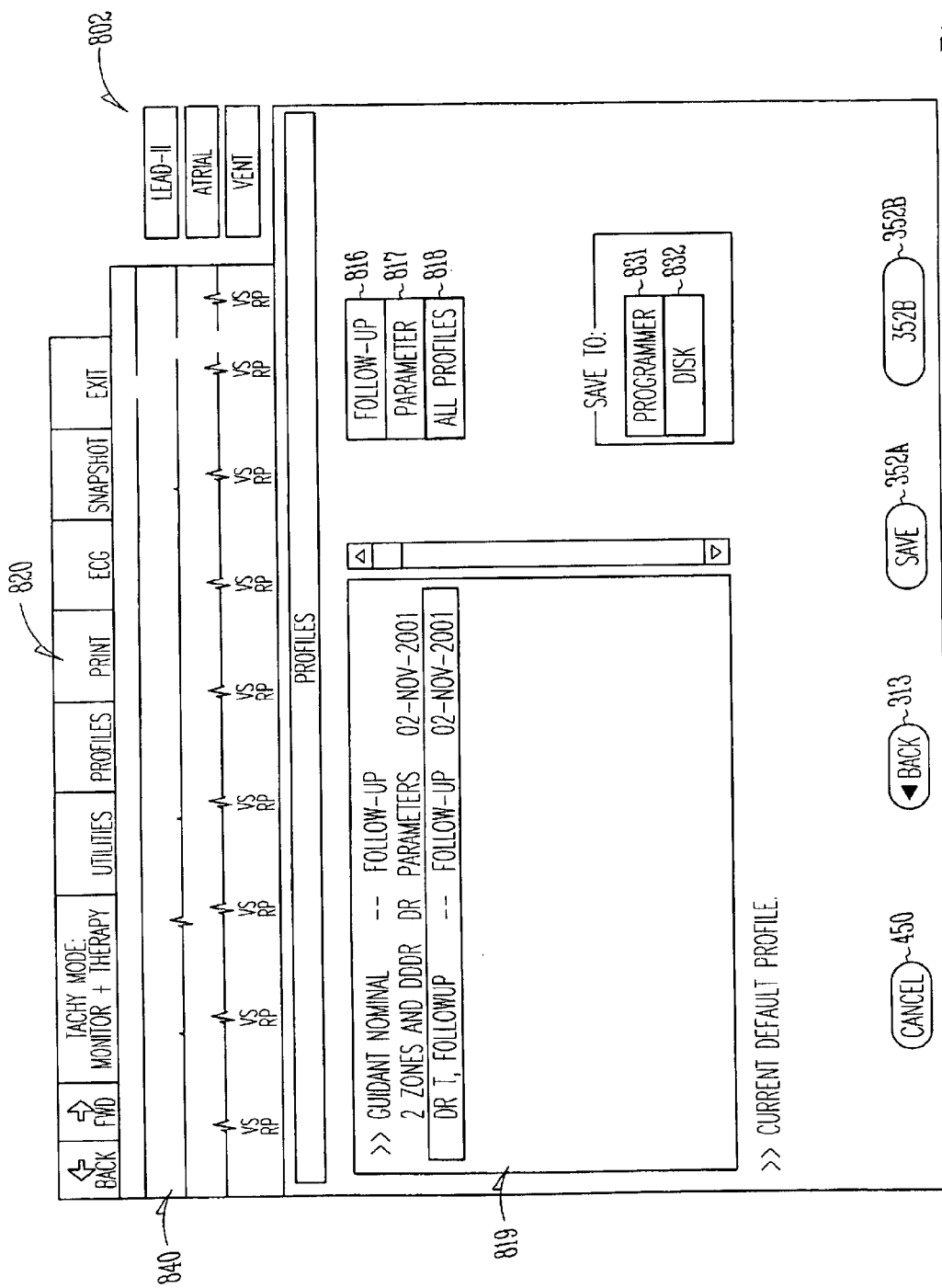
FIG. 8 is a view illustrating a further navigational interface according to an embodiment of the present system.

The embodiment shown in FIG. 7A has the Magnet/Beeper button 711 selected. Accordingly, a sub-set of input fields that are associated with magnet and beeper (or sound) parameters of the CRM device are displayed at 720. These input fields include enable magnet use, change tachy mode with magnet, beep during capacitor charge, beep on sensed and paced ventricular events, and beep when ERI is reached. In an embodiment, the magnet input fields are not displayed with the sound, i.e., beep, input fields. Thus, another control button is added to display either the magnet or sound input fields.

FIG. 7B shows the interface 702 with the episodes/EGM button 712 selected; accordingly a sub-set of input fields associated with episode storage parameters are displayed at 720. These input fields include inputs for dividing the episode memory between tachy data and brady data. Also displayed at 720 are the time durations associated with the parameters input into the tachy and brady storage input fields. These input fields further include electrocardiogram storage for atrial, ventricular and shock sources for data. Additional features having input fields displayed at 720 include nonsustained episode storage, VF priority protection, onset EGM, PMT episode storage. These input fields represent a sub-set of programmable parameters for a parameter profile for a CRM device.

Figure 7C:
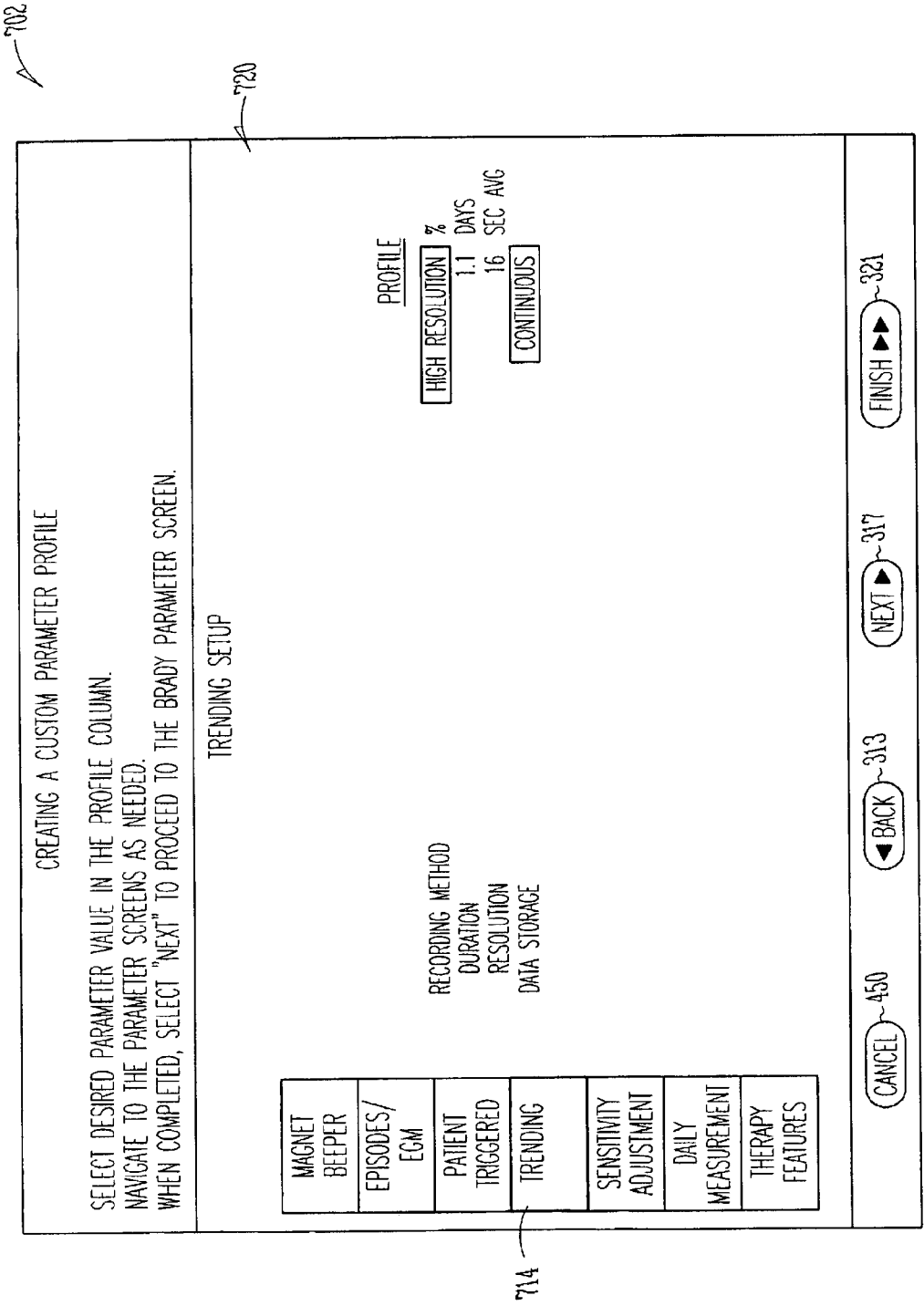

FIG. 7C shows the interface 702 with the trending button selected. A sub-set of input fields, each related to trending parameters is displayed at 720. These input fields include recording method input field, duration input field, resolution input field, and data storage input field.

FIG. 7D shows the interface 702 with the sensitivity button selected. A sub-set of the input fields, each relating to sensitivity parameters, is displayed at 720. These input fields include atrial and ventricular sensitivity input fields.

FIG. 7E shows the interface 702 with the daily measurement button selected. A sub-set of the input fields, each relating to daily measurement parameters, is displayed at 720. These input fields include atrial intrinsic amplitude on/off, atrial intrinsic amplitude maximum, atrial intrinsic amplitude minimum, ventricular intrinsic amplitude on/off, ventricular intrinsic amplitude maximum, ventricular intrinsic amplitude minimum, atrial pace impedance on/off, atrial pace impedance maximum, atrial pace impedance minimum, ventricular impedance on/off, ventricular pace impedance maximum, ventricular pace impedance minimum, shock impedance on/off, shock impedance maximum, and shock impedance minimum.

Figure 7F:
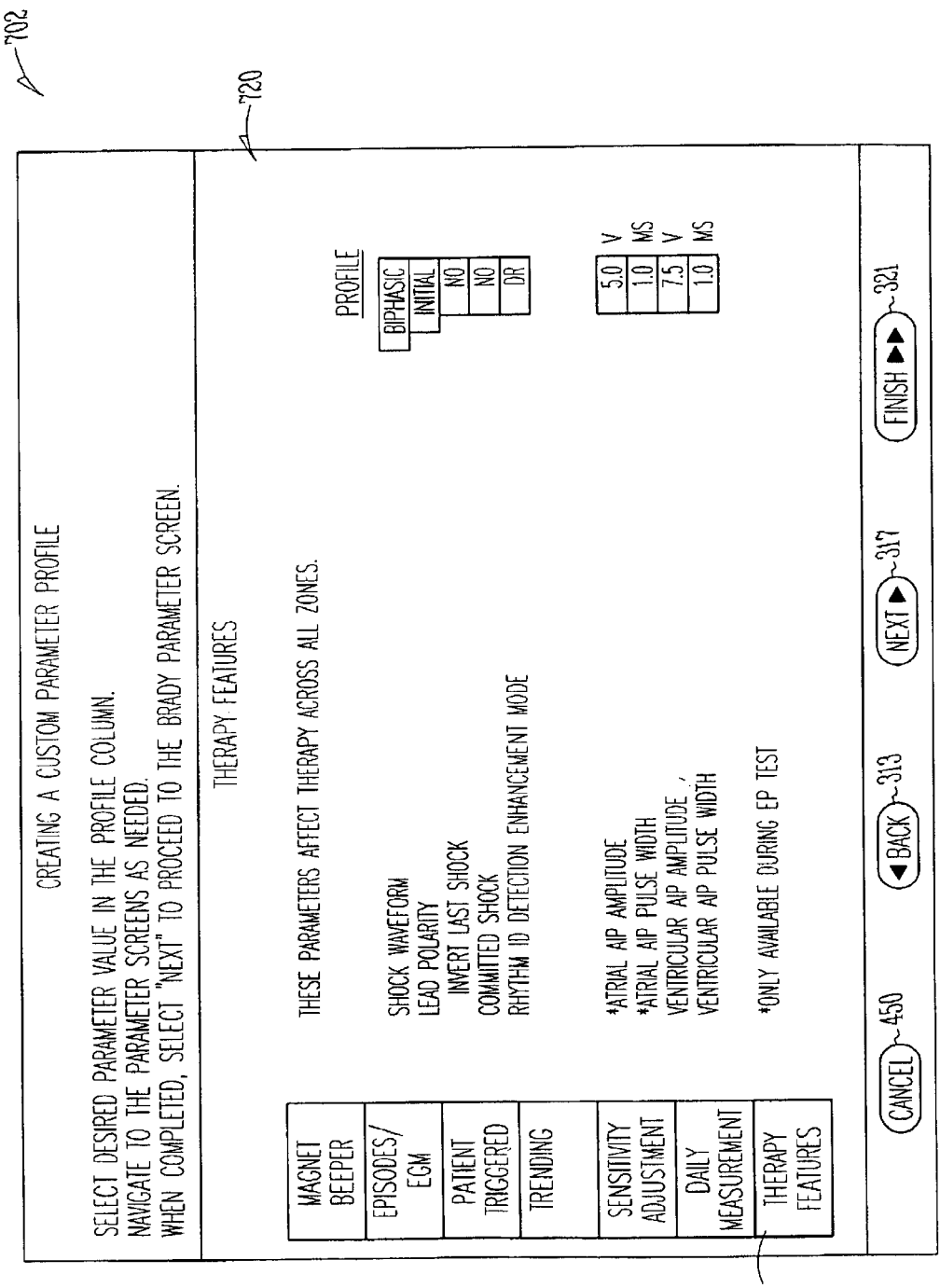

FIG. 7F shows the interface 702 with the therapy features button 718 selected. A sub-set of the input fields, each relating to therapy feature parameters, is displayed at 720. These input fields include shock waveform, lead polarity, invert last shock, committed shock, rhythm ID detection enhancement mode, atrial ATP amplitude, atrial ATP pulse width, ventricular ATP amplitude, ventricular ATP amplitude, and ventricular ATP pulse width.

The interface 702 also includes the cancel button 450, the back button 313, the next button 317, and the finish button 321 as described herein. Back button 313, upon its activation, will return to the navigation sequence of the illustrated embodiment to the prior interface 602. The next button 317, upon its activation, forwards the navigational sequence to the next interface 802. In another embodiment, interface 702 is the last programming interface and does not have the next button 317 as same can not be activated to move to another programming interface. The finish button 321, upon its activation, forwards the navigational sequence to the final interface 802.

Activation of the cancel button 450 in any of the interfaces returns the parameter input sequence to the start interface 402. In an embodiment, none of the parameters input up to the point of activating the cancel button 450 are saved. In an embodiment, the parameters input up to the point of activating the cancel button are temporarily saved until the user confirms that a cancel operation was desired.

FIG. 8 shows an end interface 802 in the navigational programming sequence. End interface 802 includes a plurality of function buttons 820 at the top of the interface. Each of these buttons 820 performs a specified function as indicated thereon. Interface 802 includes a waveform display 840 that is the same as display 440 as described herein. Interface 802 includes a display area 819 that lists certain data based on which of the selection buttons 816, 817, 818 are selected. The user selects button 816 and a list of follow-up profiles stored in the memory of the programmer are displayed in area 819. The user selects button 817 and a list of the parameter, no-follow-up profiles are listed in area 819. In the illustrated embodiment, button 818 is selected and all stored profiles in the programmer are listed in area 819. The lists of profiles displayed in area 819 include the name assigned to a profile, the type of profile, here shown as DR or VR, profile type, here shown as follow-up or parameter, and the date and time of the profile creation. The interface 802 further includes a save to buttons 831, 832, which when selected determine where the profile currently being programmed or selected in display area 819 will be saved. In the illustrated embodiment, the programmer "save to" button 831 is selected. Accordingly, the profile will be saved in the memory of the programmer upon activation of the save button 352A or save as button 352B. If the save as button 352B is activated, then the user would then be prompted to enter a profile name or confirm a replacement of a profile having a same name as would be understood by one of ordinary skill. Interface 802 further includes the cancel button 450 and the back button 313, which operate as described herein.

FIGS. 9A–9D show a sequence of follow-up profile interfaces 902A–902D that are sequentially linked together by the next buttons button 917A–917C and linked in reverse order by back buttons 913D–913B. Thus, a user must sequentially proceed through the interfaces 902A, 902B, 902C and 902D in the order or reverse order listed. For example, the next button 917A of interface 902A will navigate the user only to interface 902B. Next button 917B of interface 902B will only navigate the user to interface 902C, and so on. The next button 917D of interface 902D is, in an embodiment, not actuatable and will not navigate the user to any other screen if selected. The back button 913D of interface 902D when activated will navigate the user only to interface 902C. The back button 902C when activated will navigate the user only to interface 902B, and so on. The back button 902A on interface 902A when activated will return the programming sequence to the start interface 402. The follow-up programming sequence first interface 902A displayed when the follow-up button 412 is selected and the begin button 302 is activated. Both follow-up button 412 and begin button 302 are on start interface 402.

Interfaces 902A–902D all include a cancel button 450. Activating the cancel button 450 ends the follow-up profile programming and return the user to the start interface 402. In an embodiment, any follow-up parameters that were input into prior to activating the cancel button 450 are not saved.

Interfaces 902A–902D all include a finish button 321. Activating the finish button 321 bypasses any subsequent follow-up interfaces and proceeds directly to the end interface 802. The previously input follow-up parameters are then saved in a profile at the end interface 802.

The entire set of programmable follow-up parameters are divided into sub-sets. At least one sub-set is displayed on each interface 902A–902D. Thus, in the described embodiment, the follow-up parameters are divided into at least four sub-sets. In an embodiment, the follow-up parameters are divided into four sub-sets and input fields for one of the sub-sets are displayed on a corresponding one of the interfaces 902A–902D.

In the navigational sequence according to the teachings of the present system, if an input field is critical to the parameter profile of the selected type of therapy, then the interface on which the input field appears will remain displayed until the required parameter value is entered into the input field. In one embodiment of the present system, attempting to further navigate the sequence of interfaces without inputting the required parameter value into the input field will result in a warning message being displayed on the screen 202. In another embodiment, the navigational sequence will enter nominal values for any required parameter that is not programmed by the user.

It is one aspect of the present system to provide a limited number of input fields on an interface or sub-interface at one time. This is accomplished by the use of selection buttons that only display input fields associated with one button. For example, the input fields associated with trending parameters are displayed on interface 702 when trending selection button 714 is selected (FIG. 7). Likewise, the input fields associated with therapy feature parameters are displayed on interface 702 when therapy features selection button 718 is selected. Providing a limited number of input fields removes the input fields that are not the focus of a current parameter programming task. These input fields may be subsequently displayed on the same interface by selecting a different button or by moving to a subsequent interface. Limiting the number of parameter input fields displayed at a single time helps focus the programmer on the specific programming task at hand before moving on to other programming features. Further, limiting the number of parameter input fields displayed at a single time assists in teaching how to program in the parameters by breaking down the numerous parameters into focused segments or sub-sets of the parameters associated with a medical therapy device.

Although specific embodiments have been illustrated and described herein, it will be appreciated by those of ordinary skill in the art that any arrangement which is calculated to achieve the same purpose may be substituted for the specific embodiments shown and described. This application is intended to cover any adaptations or variations of the present system, including and not limited to changes in hardware and software, without departing from the scope of the present system. Moreover, one of ordinary skill in the art will appreciate that the invention can be implemented in a procedural design environment or any other design environment that provides the required relationships. One of skill in the art, upon reading the present disclosure, will further appreciate that the names of the methods and apparatus are not intended to limit embodiments of the system. Furthermore, additional methods and apparatus can be added to the components, functions can be rearranged among the components, and new components to correspond to future enhancements and physical devices used in embodiments of the system can be introduced without departing from the scope of the present invention. One of skill in the art will readily recognize that embodiments of the system are applicable to future medical device programmers.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A programmer for a cardiac rhythm management device, comprising:
   a cardiac rhythm management programming start interface;
   a plurality of sequentially linked, cardiac rhythm management programming interfaces each having at least one input field for receiving a programmable parameter, the programming interfaces including linked parameter programming sub-interfaces related by cardiac rhythm management function; and
   a cardiac rhythm management programming end interface.

2. The programmer of claim 1, wherein the programmer includes a set of programmable parameters for a cardiac rhythm management device, and wherein at least one of the plurality of sequentially linked programming interfaces includes a subset of the programmable parameters for a cardiac rhythm management device.

3. The programmer of claim 2, wherein the subset includes programmable parameters related to heart rhythm detection.

4. The programmer of claim 2, wherein the subset includes programmable parameters related to heart pacing.

5. The programmer of claim 2, wherein the subset includes programmable parameters related to Tachy response.

6. The programmer of claim 2, wherein the subset includes programmable parameters related to rate enhancement.

7. The programmer of claim 2, wherein the subset includes programmable parameters related to noise response.

8. The programmer of claim 2, wherein the subset includes programmable parameters related to AV delay.

9. The programmer of claim 2, wherein the subset includes programmable parameters related to data storage control.

10. The programmer of claim 1, wherein the start interface includes a link connecting the start interface to a first of the plurality of programming interfaces.

11. The programmer of claim 1, wherein each programming interface includes a link to a subsequent interface.

12. The programmer of claim 1, wherein each programming interface includes a link to a prior interface.

13. The programmer of claim 1, wherein each programming interface includes a link to the end interface.

14. The programmer of claim 1, wherein a last of the programming interfaces includes a link to the end interface.

15. The programmer of claim 1, wherein the input fields include input fields for at least one of cardiac rhythm management mode, atrial tachycardia response, lower heart rate limit, maximum tracking rate, maximum sensor rate, AV delay, atrial pulse width, atrial amplitude, atrial refractory, ventricular pulse width, ventricular amplitude, ventricular refractory, post-shock delay, sensor parameters, tachy response parameters, refractory parameters, rate enhancement parameters, noise response parameters, magnet parameters, audio parameters, episode parameters, EGM parameters, patient triggered event parameters, trending parameters, sensitivity parameters, daily measurement parameters, and therapy features parameters.

16. The programmer of 1, wherein the start interface, the plurality of programming interfaces and the end interface are graphical user interfaces.

17. The programmer of claim 1, wherein the start interface includes a link to a first linked parameter programming interface.

18. A programmer for a cardiac rhythm management device, comprising:
   a cardiac rhythm management programming start interface;
   a plurality of sequentially linked, cardiac rhythm management programming interfaces each having at least one input field for receiving a programmable parameter;
   a cardiac rhythm management programming end interface; and
   wherein the programming intrfaces include at least one linked sub-interface, the sub-interface including subsets of the programmable parameters related by cardiac rhythm management function, and wherein the at least one input field is related to a function subset of the cardiac rhythm management device.

19. The programmer of claim 18, wherein the subset for a first of the programming interfaces relates to Brady parameters.

20. The programmer of claim 18, wherein the subset for a first of the programming interfaces relates to Tachy parameters.

21. The programmer of claim 18, wherein the subset for a first of the programming interfaces relates to heart activity detection.

22. A cardiac therapy system, including:
   a cardiac rhythm management device adapted to provide a cardiac therapy to a person in response to programmed parameters within the cardiac rhythm management device; and
   a cardiac rhythm management device programmer, comprising:
      a start interface;
      a plurality of sequentially linked programming interfaces each having at least one input field for receiving a programmable parameter, the programming interfaces including at lest one linked sub-interface grouped by cardiac rhythm management function; and an end interface.

23. The system of claim 22, wherein the start interface provides a selection between current programmed parameters and nominal parameters.

24. The system of claim 23, wherein the nominal parameters are stored in the programmer.

25. The medical system of claim 23, wherein the medical device programmer includes means for remotely communicating with the medical device.

26. The medical system of claim 23, wherein the medical device programmer includes communicating system that transmits to the medical device.

27. A method of configuring a parameter profile for a cardiac rhythm management device, comprising:

displaying a start interface;

querying the user to start programming at least one parameter into a profile;

upon the user indicating a start to programming a profile, displaying a first of a plurality of sequentially linked parameter programming interfaces, each parameter programming interface containing at least one parameter input field, the programming interfaces including at least one linked parameter programming sub-interface linked by cardiac rhythm management function;

providing a back navigation button on a displayed parameter programming interface, activation of the back navigation button causes a prior interface to be displayed; and providing a next navigation button on a displayed parameter programming interface, activation of the next navigation button causes a next interface to be displayed.

28. The method according to claim 27, wherein displaying the parameter programming interface includes sequentially displaying a plurality of parameter programming interfaces upon the user repeatedly activating the next navigational button.

29. The method according to claim 28, wherein displaying the plurality of parameter programming interfaces includes each programming interface displaying distinct parameters for a cardiac rhythm management device.

30. The method of claim 29, wherein displaying cardiac rhythm management parameters includes displaying at least one parameter input field for cardiac rhythm management mode, atrial tachycardia response, lower heart rate limit, maximum tracking rate, maximum sensor rate, AV delay, atrial pulse width, atrial amplitude, atrial refractory, ventricular pulse width, ventricular amplitude, ventricular refractory, and post-shock delay.

31. The method of claim 27, wherein displaying the parameter programming interface includes providing a plurality of selection buttons and selecting one of the buttons provides a first set of parameter input fields associated with cardiac rhythm management.

32. The method of claim 31, wherein selecting one button includes displaying the first set of parameter input fields associated with cardiac rhythm management that are distinct from other sets of parameter input fields.

33. The method of claim 32, wherein the first set of parameter input fields are related to a single programmable topic the single programmable topic is separate from remaining programmable parameters.

34. The method of claim 32, wherein providing a plurality of selection buttons includes providing at least one selection button that causes the present interface to display parameter input fields associated with at least one of a type of cardiac rhythm management device setting, sensor parameters, AV delay parameters, tachy response parameters, refractory parameters, rate enhancement parameters, noise response parameters, magnet parameters, audio parameters, episode parameters, EGM parameters, patient triggered event parameters, trending parameters, sensitivity parameters, daily measurement parameters, and therapy features parameters.

35. The method of claim 27, wherein displaying a parameter programming interface includes displaying a finish navigational button, activation of the finish navigational button causes an end interface to be displayed.

36. The method of claim 35, wherein displaying a finish navigational button includes saving all input parameter values into a profile only from the end interface.

37. The method of claim 27, wherein displaying the first of a plurality of sequentially linked parameter programming interfaces includes displaying parameter input fields that are all associated with one area of operation of a cardiac rhythm management device.

38. A method of configuring a parameter profile for a cardiac rhythm management device, comprising:

querying the user to start programming at least one parameter into a profile;

upon the user indicating a start to programming a profile, displaying a first of a plurality of sequentially linked parameter programming interfaces, each parameter programming interface containing at least one parameter input field, the programning interfaces including linked sub-interfaces including parameters related by cardiac rhythm management function; and providing a next navigation button on a displayed parameter programming interface, activation of the next navigation button causes a next, sequential interface to be displayed.

39. The method according to claim 38, wherein displaying the parameter programming interface includes sequentially displaying a plurality of parameter programming interfaces upon repeated activation of the next navigational button.

40. The method of claim 39, wherein the method further includes providing a cancel navigation but on a displayed parameter programming interface, activation of the cancel button causes a first interface to be displayed.

* * * * *

UNITED STATES PATENT AND TRADEMARK OFFICE
CERTIFICATE OF CORRECTION

PATENT NO. : 6,842,644 B2 Page 1 of 1
APPLICATION NO. : 10/008525
DATED : January 11, 2005
INVENTOR(S) : Anderson et al.

It is certified that error appears in the above-identified patent and that said Letters Patent is hereby corrected as shown below:

In column 16, line 42, in Claim 18, delete "intrfaces" and insert -- interfaces --, therefor.

In column 17, line 1, in Claim 22, delete "lest" and insert -- least --, therefor.

In column 18, line 7, in Claim 33, insert -- , -- before "the".

In column 18, line 42, in Claim 38, delete "programning" and insert -- programming --, therefor.

In column 18, line 54, in Claim 40, delete "but" and insert -- button --, therefor.

Signed and Sealed this

Seventeenth Day of April, 2007

JON W. DUDAS
*Director of the United States Patent and Trademark Office*